United States Patent
Stoltz et al.

(10) Patent No.: US 10,106,479 B2
(45) Date of Patent: Oct. 23, 2018

(54) ASYMMETRIC CATALYTIC DECARBOXYLATIVE ALKYL ALKYLATION USING LOW CATALYST CONCENTRATIONS AND A ROBUST PRECATALYST

(71) Applicant: California Institute of Technology, Pasadena, CA (US)

(72) Inventors: Brian M. Stoltz, San Marino, CA (US); Alexander N. Marziale, Basel (CH); Robert A. Craig, Stanford, CA (US); Douglas Duquette, Los Angeles, CA (US); Kelly E. Kim, Pasadena, CA (US); Marc Liniger, Baden (CH); Yoshitaka Numajiri, Kamakura (JP)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/081,157

(22) Filed: Mar. 25, 2016

(65) Prior Publication Data

US 2016/0280623 A1    Sep. 29, 2016

Related U.S. Application Data

(60) Provisional application No. 62/139,522, filed on Mar. 27, 2015.

(51) Int. Cl.

| C07D 211/94 | (2006.01) |
|---|---|
| C07C 45/65 | (2006.01) |
| C07D 223/10 | (2006.01) |
| C07D 317/72 | (2006.01) |
| B01J 31/04 | (2006.01) |

(52) U.S. Cl.
CPC .............. *C07C 45/65* (2013.01); *B01J 31/04* (2013.01); *C07D 211/94* (2013.01); *C07D 223/10* (2013.01); *C07D 317/72* (2013.01); *B01J 2231/44* (2013.01); *B01J 2531/004* (2013.01); *C07C 2601/14* (2017.05); *C07C 2601/18* (2017.05); *C07C 2601/20* (2017.05); *C07C 2602/10* (2017.05)

(58) Field of Classification Search
CPC ................................................... C07D 211/94
See application file for complete search history.

(56) References Cited

U.S. PATENT DOCUMENTS

| 2,886,487 | A | 5/1959 | Kupferberg |
|---|---|---|---|
| 5,591,769 | A | 1/1997 | Himmelsbach et al. |
| 8,822,679 | B2 | 9/2014 | Stoltz et al. |
| 2006/0084820 | A1 | 4/2006 | Behenna et al. |
| 2010/0298293 | A1 | 11/2010 | Allerheiligen et al. |
| 2013/0267699 | A1 | 10/2013 | Stoltz et al. |
| 2015/0105552 | A1 | 4/2015 | Stoltz et al. |
| 2016/0096810 | A1 | 4/2016 | Stoltz et al. |
| 2016/0176773 | A1 | 6/2016 | Stoltz et al. |
| 2016/0280623 | A1 | 9/2016 | Stoltz et al. |

FOREIGN PATENT DOCUMENTS

| DE | 668489 C | 12/1938 |
|---|---|---|
| WO | WO-2003/062265 | 7/2003 |
| WO | WO-2005/012320 A2 | 2/2005 |
| WO | WO-2009/013390 A1 | 1/2009 |
| WO | WO-2009/153178 A2 | 12/2009 |
| WO | WO-2011/153509 A1 | 12/2011 |

OTHER PUBLICATIONS

Amat et al., "Enantioselective Synthesis of 3,3-Disubstituted Piperidine Derivatives by Enolate Dialkylation of Phenylglycinol-derived oxazolopiperidone Lactams," J. Org. Chem., 72:4431-4439 (2007).
Bach, T., "Regioselective Reducing Ring Opening of 2-(2-Hydroxyphenyl)-3-[(trimethylsilyl)oxy]oxetanes at the More Substituted C-2-Position", No. 7 (1997).
Badillo et al., "Enantioselective synthesis of substituted oxindoles and spirooxindoles with applications in drug discovery," Current Opinion in Drug Discovery & Development, 13(6):758-776 (2010).
Baussanne et al., "Diastereoselective Bis-Alkylation of Chiral Non-Racemic α,β-Unsaturated γ-Lactams," Tetrahedron Letters, 35(23):3931-3934 (1994).
Behenna and Stoltz, "The Enantioselective Tsuji Allylation," J. Am. Chem. Soc., 126(46):15044-15045 (2004).

(Continued)

*Primary Examiner* — Bruck Kifle
(74) *Attorney, Agent, or Firm* — Foley Hoag LLP

(57) ABSTRACT

This invention provides efficient and scalable enantioselective methods that yield 2-alkyl-2-allylcycloalkyanone compounds with quaternary stereogenic centers. Methods include the method for the preparation of a compound of formula (I):

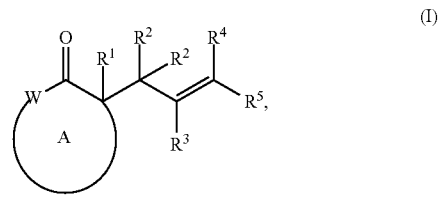

comprising treating a compound of formula (II) or (III):

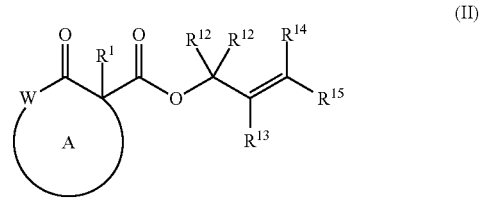

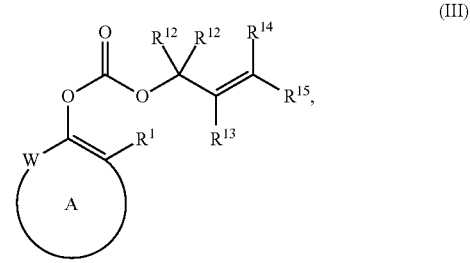

with a palladium (II) catalyst under alkylation conditions.

12 Claims, No Drawings

(56) References Cited

OTHER PUBLICATIONS

Behenna et al., "Enantioselective construction of quaternary N-heterocycles by palladium-catalysed decarboxylative allylic alkylation of lactams", Nature Chem. 2012, 4, 130.
Behenna et al., "Enantioselective Decarboxylative Alkylation Reactions: Catalyst Developement, Substrate Scope, and Mechanistic Studies", Chem. Eur. J. 2011, 17, 14199.
Bennett et al., "A Unified Approach to the Daucane and Sphenolobane Bicyclo[5.3.0]decane Core: Enantioselective Total Synthesis of Daucene, Daucenal, Epoxydaucenal B, and 14-para-Anisoyloxydauc-4,8-diene", Chem. Eur. J. 2013, 52, 17745.
Bennett et al., "Expanding Insight into Asymmetric Palladium-Catalyzed Allylic Alklation of N-Heterocyclic Molecules and Cyclic Ketones", Chem. Eur. J. 2013, 19, 4414.
Bennett et al., Synthesis of enantioenriched γ-quaternary cycloheptenones using a combined allylic alkylation/Stork-Danheiser approach: preparation of mono-, bi-, and tricyclic systems, Org. Biomol. Chem., 10(1):56-9 (2012).
Bobranski et al., Hydration of Phenyldiallylacetamide, 7, Bulletin De L'Academie Polonaise De Sciences, Serie Des Sciences, Chimiques, Geologiques Et Geographiques, pp. 399-401 (1959) (CAS Abstract).
Bulman et al., "Short and Versatile Route to a Key Intermediate for Lactacystin Synthesis", Organic Letters, vol. 5, No. 3, pp. 353-355 (2003).
Coates et al., "Efficient synthesis of 3-substituted lactams using Meerwein Eschenmoser Claisen [3,3] sigmatropic rearrangements", 32(33) Tetrahedron Letts. 4199-202 (1991) (CAS Abstract).
Day et al., "The Catalytic Enantioselective Total Synthesis of (+)-Liphagal," Angew. Chem. Int. Ed., 50:6814-6818 (2011).
Desmaele et al., "Stereocontrolled Elaboration of Quaternary Carbon Centers through the Asymmetric Michael-Type Alkylation of Chiral Imines/Secondary Enamines: Enantioselective Synthesis of (+)-Vincamine," J. Org. Chem., 62:3890-3901 (1997).
Enders et al., "Asymmetric Electrophilic Substitutions at the α-Position of γ- and δ-Lactams," Eur. J. Org. Chem., pp. 4463-4477 (2001).
Enquist and Stoltz, "The total synthesis of (−)-cyanthiwigin F by means of double catalytic enantioselective alkylation," Nature, 453:1228-1231 (2008).
Enquist et al., "Total Syntheses of Cyanthiwigins B, F, and G", Chem. Eur. J. 2011, 17, 9957.
Ezquerra et al., "Stereoselective Double Alkylation of Ethyl N-Boc-pyroglutamate," J. Org. Chem., 59(15):4327-4331 (1994).
Fuji et al., "Addition-elimination strategy for asymmetric induction: a chiral sulfoxide as a leaving group", 31 (17) Tetrahedron Letts. 2419-22 (1990) (CAS abstract).
Gartshore et al., "Enantioselective Palladium-Catalyzed Decarboxylative Allylation of Carbazolones and Indolones: Formal Synthesis of (+)-Kopsihainanine A", Angew. Chem. Int. Ed. 2013, 52, 4113.
Groaning and Meyers, "Chiral Non-Racemic Bicyclic Lactams. Auxiliary-Based Asymmetric Reactions," Tetrahedron, 56(549):9843-9873 (2000).
Helmchen and Pfaltz, "Phosphinooxazolines—A New Class of Versatile, Modular P,N-Ligands for Asymmetric Catalysis," Acc. Chem. Res., 33(6):336-345 (2000).
Hong et al., "Biosynthesis and Chemical Synthesis of Presilphiperfolanol Natural Products", Angew. Chem. Int. Ed. 2014, 53, 5248.
Hong et al., "Enantioselective Total Synthesis of the Reported Structures of (−)-9-epi-Presilphiperfolan-1-ol and (−)-Presilphiperfolan-1-ol: Structural Confirmation and Reassignment and Biosynthetic Insights", Angew. Chem. Int. Ed. 2012, 51, 9674.
Hong et al., "Palladium-catalyzed asymmetric alkylation in the synthesis of cyclopentanoid and cycloheptanoid core structures bearing all-carbon quaternary stereocenters", Tetrahedron 2011, 67, 10234.
Hong et al., "The Construction of All-Carbon Quaternary Stereocenters by Use of Pd-Catalyzed Asymmetric Allylic Alkylation Reactions in Total Synthesis", Eur. J. Org. Chem. 2013, 14, 2745.
Imao et al., "Easy Access to Esters with a Benzylic Quaternary Carbon Center from Diallyl Malonates by Palladium-Catalyzed Decarboxylative Allylation," J. Org. Chem., 72:1652-1658 (2007).
Jakubec et al., "Enantio- and diastereoselective Michael additions of C-succinimidyl esters to nitro olefins using cinchonine-derived bifunctional organocatalysts," Tetrahedron: Asymmetry, 22:1147-1155 (2011).
Jing et al., "Total Synthesis of (+)-Kopsihainanine A", Chem. Eur. J. 2012, 18, 6729.
Juaristi et al., Enantioselective synthesis of β-amino acids. Part 9: Preparation of enantiopure α,α-disubstituted β-amino acids from 1-benzoyl-2(S)-tert-butyl-3-methylperhydropyrimidin-4-one1,2, Tetrahedron: Asymmetry, 9:3881-3888 (1998).
Keith et al., "The Reaction Mechanism of the Enantioselective Tsuji Allylation: Inner-Sphere and Outer-Sphere Pathways, Internal Rearrangements, and Asymmetric C—C Bond Formation", J. Am. Chem. Soc. 2012, 134, 19050.
Kim et al., An Asymmetric Synthesis of (+)-Isonitramine by 'Triple Allylic Strain-Controlled' Intramolecular SN2' Alkylation, Tetrahedron Letters, 37(9):1433-1434 (1996).
Li et al., "Enantioselective Palladium-Catalyzed Decarboxylative Allylation of Carbazolones: Total Synthesis of (−)-Aspidospermidine and (+)-Kopsihainanine A", Angew Chem. Int. Ed. 2013, 52, 4117.
Liu et al., "Construction of Vicinal Tertiary and All-Carbon Quaternary Stereocenters via Ir-Catalyzed Regio-, Diastereo-, and Enantioselective Allylic Alkylation and Applications in Sequential Pd Catalysis", J. Am. Chem. Soc. 2013, 135, 10626.
Lu and Ma, "Metal-Catalyzed Enantioselective Allylation in Asymmetric Synthesis," Angew. Chem. Int. Ed., 47:258-297 (2008).
Ma et al., "Palladium-catalyzed decarboxylative allylic alkylation of diastereomeric β-ketoesters", Tetrahedron 2014, 70, 4208.
McDougal et al., "High-Throughput Screening of the Asymmetric Decarboxylative Alkylation Reaction of Enolate-Stabilized Enol Carbonates," Synlett, 11:1712-1716 (2010).
McDougal et al., "Rapid synthesis of an electron-deficient t-BuPHOX ligand: cross-coupling of aryl bromides with secondary phosphine oxides," Tetrahedron Letters, 51:5550-5554 (2010).
McFadden and Stoltz, "The Catalytic Enantioselective, Protecting Group-Free Total Synthesis of (+)-Dichroanone," J. Am. Chem. Soc., 128:7738-7739 (2006).
Mertes et al., "Glutarimides", J.Am.Pharma. Assoc. vol. 67, pp. 882-885, (1912-1977) (1958) (CAS Abstract).
Meyers et al., "Stereoselective Alkylations in Rigid Systems. Effect of Remote Substituents on π-Facial Additions to Lactam Enolates. Stereoelectronic and Steric Effects," J. Am. Chem. Soc., 120:7429-7438 (1998).
Mohr and Stoltz, "Enantioselective Tsuji Allylations," Chem. Asian J., 2:1476-1491 (2007).
Mohr et al., "Deracemization of Quaternary Stereocenters by Pd-Catalyzed Enantioconvergent Decarboxylative Allylation of Racemic β-Ketoesters," Angew. Chem. Int. Ed., 44:6924-6927 (2005).
Moss et al., "Catalytic Enantio- and Diastereoselective Alkylations with Cyclic Sulfamidates," Angew. Chem. Int. Ed., 49:568-571 (2010).
Numajiri et al., "Enantioselective synthesis of a-quaternary mannich adducts by palladium-catalyzed allylic alkylation: Total synthesis of (+)-sibirinine," J Am Chem Soc, 137:1040-3 (2015).
Ojima and Pei, "Asymmetric Synthesis with Chiral β-Lactams. Highly Stereoselective Alkylation and Aldol Reaction of a Chiral 3-Amino-4-Styryl-β-Lactam," Tetrahedron Letters, 31(7):977-980 (1990).
Padwa et al., "A Novel Cycloaddition Reaction of α-Diazo-γ-amido Ketones Catalyzed by Rhodium (II) Acetate. Scope and Mechanistic Details of the Process", 61(7) J. Org. Chem. 2283-92 (1996) (CAS Abstract).
Park et al., "Highly Enantioselective Phase-Transfer Catalytic α-Alkylation of α-tert-Butoxycarbonyllactams: Construction of β-Quaternary Chiral Pyrrolidine and Piperidine Systems," Adv. Synth. Catal., 353:3313-3318 (2011).
Reeves et al., "Development of (Trimethylsilyl)ethyl Ester Protected Enolates and Applications in Palladium-Catalyzed Enantioselective Allylic Alkylation: Intermolecular Cross-Coupling of Functionalized Electrophiles", Org. Lett. 2014, 16, 2314.

(56) References Cited

OTHER PUBLICATIONS

Reeves, et al., "Enantioselective Construction of α-Quaternary Cyclobutanones by Catalytic Asymmetric Allylic Alkylation", Angew. Chem. Int. Ed. 2013, 52, 6718.
Rodriguez et al., "Carba Peptide Bond Surrogates/Different Approaches to Gly-(CH2-CH2)-D,L-XAA Pseudodipeptide Units", International Journal of Peptide and Protein Research, vol. 39, No. 3, pp. 273-277 (1992).
Schwarz and Meyers, "Tandem α-Cyano Enamine/Enolate Alkylations on Bicyclic Lactams: Asymmetric Carbocycle and Heterocycle Synthesis," J. Org. Chem., 63(5):1619-1629 (1998).
Search Report from International Application No. PCT/US2012/043904 dated Feb. 1, 2013.
Seto et al., "Catalytic Enantioselective Alkylation of Substituted Dioxanone Enol Ethers: Ready Access to C(α)-Tetrasubstituted Hydroxyketones, Acids, and Esters," Angew. Chem. Int. Ed., 47:6873-6876 (2008).
Shibuya et al., "Enantioselective Synthesis of 5-6-7 Carbocyclic Core of the Gagunin Diterpenoids", Org. Lett. 2013, 15, 3480.
Streuff et al., "A palladium-catalysed enolate alkylation cascade for the formation of adjacent quaternary and tertiary sterocentres," Nature Chemistry, 2:192-196 (2010).
Takahashi et al., "Atropisomeric lactam chemistry: catalytic enantioselective synthesis, application to asymmetric enolate chemistry and synthesis of key intermediates for NET inhibitors," Tetrahedron, 66:288-296 (2010).
Tani et al., "A Facile and Modular Synthesis of Phosphinooxazoline Ligands," Organic Letters, 9(13):2529-2531 (2007).
Tari et al., "Recoverable *Cinchona* ammonium salts as organocatalysts in the enantioselective Michael addition of β-Keto esters," Tetrahedron: Asymmetry, 21:2872-2878 (2010).
Trost and Brennan, "Asymmetric Synthesis of Oxindole and Indole Spirocyclic Alkaloid Natural Products," Synthesis, 18:3003-3025 (2009).
Trost et al., "Enantioselective Synthesis of [alpha]-Tertiary Hydroxyaldehydes by Palladium-Catalyzed Asymmetric Allylic Alkylation of Enolates", Journal of the American Chemical Society, vol. 129, No. 2, pp. 282-283 (2007).
Trost, Barry M., "Asymmetric Allylic Alkylation, an Enabling Methodology," J. Org. Chem., 69(18):5813-5837 (2004).
Varea et al., "Asymmetric Synthesis. XXXVI. Synthesis of 2-Methyl 5-Substituted Piperidines from Chiral Non-racemic Lactams," Tetrahedron Letters, 36(7):1035-1038 (1995).
Vijn et al., "Highly Enantioselective Synthesis of a 2,3-Dihydroindole Mediated by N-Methylephedrine," Angew. Chem. Int. Ed. Engl., 23(2):165-166 (1984).
Weaver et al., "Transition Metal-Catalyzed Decarboxylative Allylation and Benzylation Reactions," Chem. Rev., 111:1846-1913 (2011).
White et al., "The Catalytic Asymmetric Total Synthesis of Elatol," J. Am. Chem. Soc., 130(3):810-811 (2008).
Written Opinion from International Application No. PCT/US2012/043904 dated Feb. 1, 2013.
Zhou et al., "Catalytic Asymmetric Synthesis of Oxindoles Bearing a Tetrasubstituted Stereocenter at the C-3 Position," Adv. Synth. Catal., 352:1381-1407 (2010).
International Search Report and Written Opinion for International Application No. PCT/US2016/024238 dated Jul. 11, 2016.
Sherden, "Mechanistic investigations into the palladium-catalyzed decarboxylative allylic alkylation of ketone enolates using the PHOX ligand architecture," Chapter 1, retrieved from the Internet: http://thesis.library.caltech.edu/6476/2/03-Chpt_1_Intro.pdf (2011).
Chattopadhyay et al., "Mechanistic Origin of the Stereodivergence in Decarboxylative Allylation," Org Lett, 12(13): 3042-3045 (2010).

ASYMMETRIC CATALYTIC DECARBOXYLATIVE ALKYL ALKYLATION USING LOW CATALYST CONCENTRATIONS AND A ROBUST PRECATALYST

RELATED APPLICATIONS

This Application claims the benefit of U.S. Provisional Application 62/139,522, filed Mar. 27, 2015, the content of which is incorporated herein by reference.

GOVERNMENT SUPPORT

This invention was made with government support under Grant Number GM080269, awarded by the National Institutes of Health. The government has certain rights in the invention.

BACKGROUND OF THE INVENTION

The catalytic enantioselective construction of all-carbon quaternary centers represents a considerable challenge in synthetic organic chemistry.[1,2] A new carbon-carbon bond must be formed in the face of significant steric hindrance to accomplish this goal.

Synthetic methods for the generation of quaternary stereocenters are extremely desirable given their prevalence in a broad variety of biologically active natural products.[2] Despite their importance, the number of highly enantioselective transformations that construct quaternary stereocenters under mild reaction conditions is limited. The palladium-catalyzed decarboxylative asymmetric allylic alkylation is a powerful and reliable approach to bridge this gap.[3]

However, despite the importance of palladium-catalyzed decarboxylative asymmetric alkylation in total synthesis, its application on an industrial scale is often hampered by the need for high catalyst loadings (5.0-10.0 mol %). The high cost of palladium significantly increases the cost of each reaction. Furthermore, high catalyst loadings also increase the risk of poisoning downstream chemistry or contaminating active pharmaceutical ingredients.[4]

These drawbacks have discouraged application of the enantioselective allylic alkylation on a larger scale. The application of transition metal catalysis to industry-scale synthesis requires transformations that are safe, robust, cost-effective, and scalable.[5] Consequently, there remains a significant need to develop new reaction protocols that employ lower catalyst concentrations and hence facilitate the scale-up of such transformations.

SUMMARY OF THE INVENTION

The present invention provides methods for preparing a compound of formula (I):

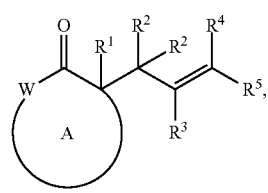

comprising treating a compound of formula (II) or (III):

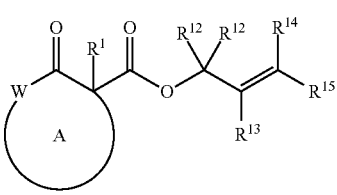

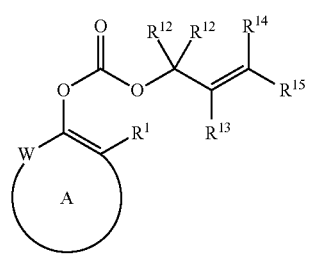

or a salt thereof;
with a Pd(II) catalyst under alkylation conditions, wherein, as valence and stability permit,
$R^1$ represents hydrogen or substituted or unsubstituted alkyl, alkenyl, alkynyl, aralkyl, aryl, heteroaralkyl, heteroaryl, (cycloalkyl)alkyl, cycloalkyl, (heterocycloalkyl)alkyl, heterocycloalkyl, alkoxy, amino, or halo;
$R^2$, $R^3$, $R^4$, $R^5$, $R^{12}$, $R^{13}$, $R^{14}$, and $R^{15}$ are independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, cycloalkyl, heterocycloalkyl, aralkyl, arylalkoxy, heteroaralkyl, (cycloalkyl)alkyl, and (heterocycloalkyl)alkyl;
W represents, as valence permits, —O—, —S—, —NR$^6$—, —CR$^7$R$^8$—, —C(O)—, —CR$^7$=, or —N=;
$R^6$ represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{10}$, —SR$^{10}$, or —NR$^{10}$R$^{11}$;
$R^7$ and $R^8$ each independently represent hydrogen, hydroxyl, halogen, nitro, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, cyano, carboxyl, sulfate, amino, alkoxy, aryloxy, arylalkoxy, alkylamino, alkylthio, hydroxyalkyl, alkoxyalkyl, aminoalkyl, thioalkyl, haloalkyl, ether, thioether, ester, amido, thioester, carbonate, carbamate, urea, sulfonate, sulfone, sulfoxide, sulfonamide, acyl, acyloxy, or acylamino;
or $R^6$, $R^7$, and $R^8$ taken together with a substituent on ring A and the intervening atoms, form an optionally substituted aryl, heteroaryl, cycloalkyl, cycloalkenyl, heterocycloalkyl, or heterocycloalkenyl group;
$R^{10}$ and $R^{11}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl; and ring A represents an optionally substituted cycloalkyl, heterocycloalkyl, cycloalkenyl, or heterocycloalkenyl group.

The present invention further provides methods for preparing a compound of formula (I):

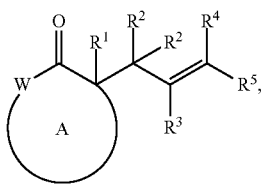

comprising treating a compound of formula (IV) or (V) or a salt thereof:

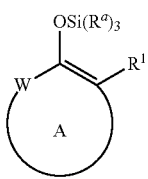

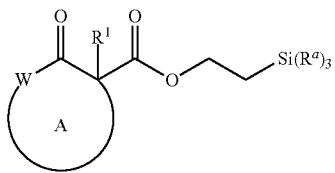

with a compound of formula (X):

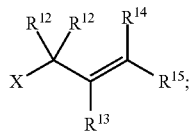

and
a Pd(II) catalyst under alkylation conditions, wherein, as valence and stability permit, $R^1$ represents hydrogen or substituted or unsubstituted alkyl, alkenyl, alkynyl, aralkyl, aryl, heteroaralkyl, heteroaryl, (cycloalkyl)alkyl, cycloalkyl, (heterocycloalkyl)alkyl, heterocycloalkyl, alkoxy, amino, or halo;

$R^2$, $R^3$, $R^4$, $R^5$, $R^{12}$, $R^{13}$, $R^{14}$, and $R^{15}$ are independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, cycloalkyl, heterocycloalkyl, aralkyl, arylalkoxy, heteroaralkyl, (cycloalkyl)alkyl, and (heterocycloalkyl)alkyl;

W represents, as valence permits, —O—, —S—, —$NR^6$—, —$CR^7R^8$—, —C(O)—, —$CR^7$=, or —N=;

$R^6$ represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —$S(O)_2$(aryl), —$S(O)_2$(alkyl), —$S(O)_2$(haloalkyl), —$OR^{10}$, —$SR^{10}$, or —$NR^{10}R^{11}$;

$R^7$ and $R^8$ each independently represent hydrogen, hydroxyl, halogen, nitro, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, cyano, carboxyl, sulfate, amino, alkoxy, aryloxy, arylalkoxy, alkylamino, alkylthio, hydroxyalkyl, alkoxyalkyl, aminoalkyl, thioalkyl, haloalkyl, ether, thioether, ester, amido, thioester, carbonate, carbamate, urea, sulfonate, sulfone, sulfoxide, sulfonamide, acyl, acyloxy, or acylamino;

or $R^6$, $R^7$, and $R^8$ taken together with a substituent on ring A and the intervening atoms, form an optionally substituted aryl, heteroaryl, cycloalkyl, cycloalkenyl, heterocycloalkyl, or heterocycloalkenyl group;

$R^{10}$ and $R^{11}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl;

ring A represents an optionally substituted cycloalkyl, heterocycloalkyl, cycloalkenyl, or heterocycloalkenyl group;

$R^a$ represents optionally substituted alkyl, aryl, or alkoxyl; and

X represents a halide, carbonate, sulfonate, acetate, or carboxylate.

DETAILED DESCRIPTION OF THE INVENTION

I. Definitions

The definitions for the terms described below are applicable to the use of the term by itself or in combination with another term.

The term "acyl" is art-recognized and refers to a group represented by the general formula hydrocarbyl-C(O)—, preferably alkyl-C(O)—.

The term "acylamino" is art-recognized and refers to an amino group substituted with an acyl group and may be represented, for example, by the formula hydrocarbyl-C(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond that is straight chained or branched and has from 1 to about 20 carbon atoms, preferably from 1 to about 10 unless otherwise defined. The term "alkenyl" is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthiols, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

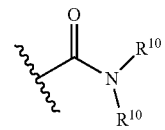

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

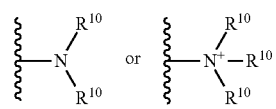

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group. An aralkyl group is connected to the rest of the molecule through the alkyl component of the aralkyl group.

The term "aryl" as used herein include substituted or unsubstituted single-ring aromatic groups in which each atom of the ring is carbon. Preferably the ring is a 5- to 10-membered ring, more preferably a 6- to 10-membered ring or a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. Exemplary substitution on an aryl group can include, for example, a halogen, a haloalkyl such as trifluoromethyl, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety The term "carbamate" is art-recognized and refers to a group

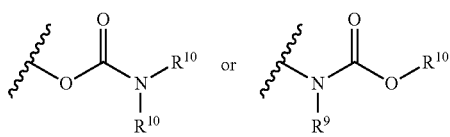

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "cycloalkylalkyl", as used herein, refers to an alkyl group substituted with a cycloalkyl group.

The term "carbonate" is art-recognized and refers to a group $-OCO_2-R^{10}$, wherein $R^{10}$ represents a hydrocarbyl group.

The term "carboxyl", as used herein, refers to a group represented by the formula $-CO_2H$.

The term "ester", as used herein, refers to a group $-C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a heteroaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include 5- to 10-membered cyclic or polycyclic ring systems, including, for example, pyrrole, furan, thiophene, imidazole, oxazole, thiazole, pyrazole, pyridine, pyrazine, pyridazine, and pyrimidine, and the like. Exemplary optional substituents on heteroaryl groups include those substituents put forth as exemplary substituents on aryl groups, above.

The term "heteroatom" as used herein means an atom of any element other than carbon or hydrogen. Preferred heteroatoms are nitrogen, oxygen, and sulfur.

The terms "heterocycloalkyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocycloalkyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocycloalkyls. Heterocycloalkyl groups include, for example, piperidine, piperazine, pyrrolidine, morpholine, lactones, lactams, and the like.

The term "heterocycloalkylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto. A "silyl ether" refers to a silyl group linked through an oxygen to a hydrocarbyl group. Exemplary silyl ethers include —OSi(CH$_3$)$_3$ (—OTMS), —OSi(CH$_3$)$_2$t-Bu (—OTBS), —OSi(Ph)$_2$t-Bu (—OTBDPS), and —OSi(iPr)$_3$ (—OTIPS).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a haloalkyl, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

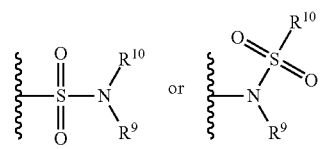

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof. In some embodiments, a sulfonate can mean an alkylated sulfonate of the formula SO$_3$(alkyl).

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

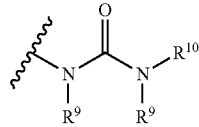

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

II. Description of the Invention.

This invention is based on the discovery of an efficient, scalable catalytic decarboxylative allylic alkylation reaction that generates cyclic cycloalkanone and lactam products having an α-stereocenter, such as lactones, thiolactones, cycloalkanones, and lactams. The decarboxylative allylic alkylation reaction is catalyzed by a robust Pd(II) catalyst and a ligand, preferably a chiral ligand, and the products can be quickly and efficiently elaborated into complex products.

According to embodiments of the present invention, a wide range of structurally-diverse, functionalized products are prepared by a readily scalable stereoselective method of palladium-catalyzed enantioselective enolate allylic alkylation. This chemistry is useful in the synthesis of bioactive alkaloids, and for the construction of novel building blocks for medicinal and polymer chemistry.

Indeed, in some embodiments of the present invention, a method of making a building block compound comprises reacting a substrate compound with a ligand in the presence of a palladium-based catalyst and a solvent. The palladium-based catalysts, ligands and solvents useful in this reaction are described in more detail below in Section III.

III. Methods of the Invention

In certain aspects, the present invention provides a method for preparing a compound of formula (I):

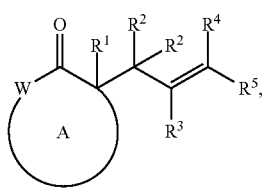
(I)

comprising treating a compound of formula (II) or (III):

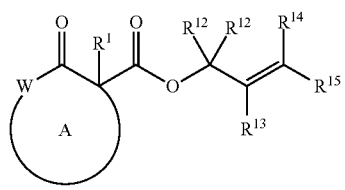
(II)

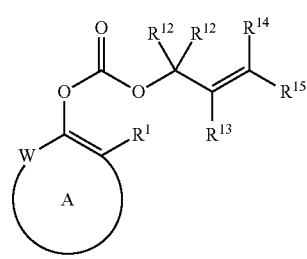
(III)

or a salt thereof;
with a Pd(II) catalyst under alkylation conditions, wherein, as valence and stability permit,
$R^1$ represents hydrogen or substituted or unsubstituted alkyl, alkenyl, alkynyl, aralkyl, aryl, heteroaralkyl, heteroaryl, (cycloalkyl)alkyl, cycloalkyl, (heterocycloalkyl)alkyl, heterocycloalkyl, alkoxy, amino, or halo;

$R^2$, $R^3$, $R^4$, $R^5$, $R^{12}$, $R^{13}$, $R^{14}$, and $R^{15}$ are independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, cycloalkyl, heterocycloalkyl, aralkyl, arylalkoxy, heteroaralkyl, (cycloalkyl)alkyl, and (heterocycloalkyl)alkyl;

W represents, as valence permits, —O—, —S—, —NR$^6$—, —CR$^7$R$^8$—, —C(O)—, —CR$^7$=, or —N=;

$R^6$ represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{10}$, —SR$^{10}$, or —NR$^{10}$R$^{11}$;

$R^7$ and $R^8$ each independently represent hydrogen, hydroxyl, halogen, nitro, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, cyano, carboxyl, sulfate, amino, alkoxy, aryloxy, arylalkoxy, alkylamino, alkylthio, hydroxyalkyl, alkoxyalkyl, aminoalkyl, thioalkyl, haloalkyl, ether, thioether, ester, amido, thioester, carbonate, carbamate, urea, sulfonate, sulfone, sulfoxide, sulfonamide, acyl, acyloxy, or acylamino;

or $R^6$, $R^7$, and $R^8$ taken together with a substituent on ring A and the intervening atoms, form an optionally substituted aryl, heteroaryl, cycloalkyl, cycloalkenyl, heterocycloalkyl, or heterocycloalkenyl group;

$R^{10}$ and $R^{11}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl; and ring A represents an optionally substituted cycloalkyl, heterocycloalkyl, cycloalkenyl, or heterocycloalkenyl group.

In certain embodiments, the compound of formula (I) is represented by formula (Ia):

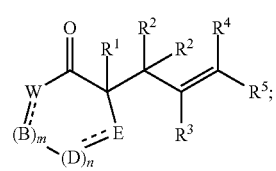
(Ia)

and
the compound of formula (II) is represented by formula (IIa):

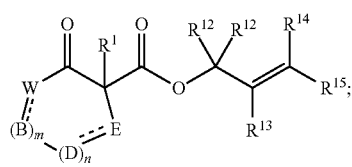
(IIa)

and
the compound of formula (III) is represented by formula (IIIa):

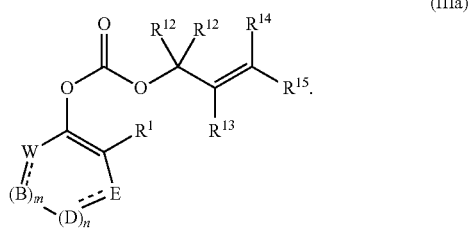

In certain such embodiments, B, D, and E each independently for each occurrence represent, as valence permits, —O—, —S—, —NR$^6$—, —CR$^7$R$^8$—, —C(O)—, —CR$^7$=, or —N=; provided that no two adjacent occurrences of W, B, D, and E are NR$^6$, O, S, or N;

or any two occurrences of R$^6$, R$^7$, and R$^8$ on adjacent W, B, D, or E groups, taken together with the intervening atoms, form an optionally substituted aryl, heteroaryl, cycloalkyl, cycloalkenyl, heterocycloalkyl, or heterocycloalkenyl group;

each occurrence of === independently represents a double bond or a single bond as permitted by valence; and m and n are integers each independently selected from 0, 1, and 2.

In certain embodiments, W represents —O—, —S—, —NR$^6$—, —CR$^7$R$^8$— or —CR$^7$=.

In certain embodiments, the sum of m and n is 0, 1, 2, or 3; that is, ring A is a 4-7 membered ring.

In certain embodiments, ring A is a carbocyclic ring.

In certain such embodiments, each occurrence of W, B, D, and E is independently —CR$^7$R$^8$—, or —CR$^7$—, or —C(O)—. For example, one occurrence of W, B, D, and E may be —CR$^7$R$^8$— or —C(O)—, while the remaining three may be —CR$^7$R$^8$—. In certain such embodiments, R$^7$ and R$^8$, independently for each occurrence, are selected from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, arylalkoxy, alkylamino, and amido.

In certain embodiments, ring A contains one or more double bonds, e.g., one or more carbon-carbon double bonds.

In certain such embodiments, at least two adjacent occurrences of W, B, D, and E are —CR$^7$—. For example, W and B may each be —CR$^7$— while m is 1. In certain such embodiments, R$^7$ is independently selected for each occurrence from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, alkylamino, amido, and acylamino; or the occurrence of R$^7$ on W and the occurrence of R$^7$ on B are taken together to form an optionally substituted aryl, heteroaryl, cycloalkenyl, or heterocycloalkenyl group. In further such embodiments, the occurrence of R$^7$ on W and the occurrence of R$^7$ on B are taken together to form an optionally substituted aryl, heteroaryl, cycloalkenyl, or heterocycloalkenyl group, preferably an optionally substituted aryl group. For example, ring A may be a tetralone-derived substrate.

Alternatively, in certain embodiments in which W and B are each —CR$^7$—, the occurrence of R$^7$ on W is selected from amino, alkylamino, amido, acylamino, and N-bound heterocycloalkyl.

In alternative embodiments, at least one occurrence of W, B, D, and E is —NR$^6$—. For example, W may be —NR$^6$—. In certain such embodiments, at least one occurrence of the remaining B, D, and E is —NR$^6$— or —O—. In further such embodiments, R$^6$ represents, independently for each occurrence, hydrogen or optionally substituted alkyl, aralkyl, heteroaralkyl, —C(O)alkyl, —C(O)aryl, —C(O)aralkyl, —C(O)O(alkyl), —C(O)O(aryl), —C(O)O(aralkyl), or —S(O)$_2$(aryl).

In certain embodiments, at least one occurrence of W, B, D, and E is —O—.

In certain embodiments, R$^2$, R$^3$, R$^4$, R$^5$, R$^{12}$, R$^{13}$, R$^{14}$, and R$^{15}$ are each independently selected for each occurrence from hydrogen, halogen, cyano, alkyl, alkoxy, alkylthio, amide, amine, aryloxy, and arylalkoxy. For example, R$^2$, R$^3$, R$^4$, R$^5$, R$^{12}$, R$^{13}$, R$^{14}$, and R$^{15}$ are each independently hydrogen or lower alkyl. Preferably, R$^2$, R$^3$, R$^4$, R$^5$, R$^{12}$, R$^{13}$, R$^{14}$, and R$^{15}$ are each hydrogen.

In certain embodiments, R$^1$ represents substituted or unsubstituted alkyl, alkenyl, alkynyl, aralkyl, aryl, heteroaralkyl, heteroaryl, (cycloalkyl)alkyl, cycloalkyl, (heterocycloalkyl)alkyl, heterocycloalkyl, or halo.

In certain embodiments, R$^1$ represents substituted or unsubstituted alkyl, alkenyl, alkynyl, aralkyl, aryl, heteroaralkyl, (cycloalkyl)alkyl, (heterocycloalkyl)alkyl, heterocycloalkyl, or halo. In certain such embodiments, R$^1$ is selected from optionally substituted alkyl, aryl, aralkyl, haloalkyl, alkoxyalkyl, and hydroxyalkyl. For example, R$^1$ may be alkyl, optionally substituted with halo, hydroxy, alkoxy, aryloxy, arylalkoxy, cyano, nitro, azido, —CO$_2$H, —C(O)O(alkyl), amino, alkylamino, arylamino, aralkylamino, and amido.

In certain embodiments, the method for preparing a compound of formula (I) comprises treating a compound of formula (II) with a Pd(II) catalyst under alkylation conditions.

In certain embodiments, the method for preparing a compound of formula (I) comprises treating a compound of formula (III) with a Pd(II) catalyst under alkylation conditions.

In certain embodiments, the method yields a compound of formula (I) that is enantioenriched.

In further aspects, the present invention provides a method for preparing a compound of formula (I), described above, comprising treating a compound of formula (IV) or (V) or a salt thereof:

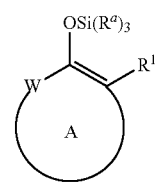

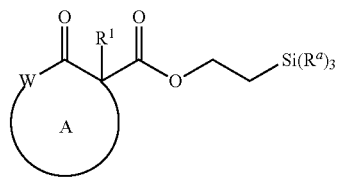

with a compound of formula (X):

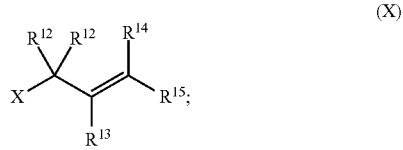

and
a Pd(II) catalyst under alkylation conditions, wherein, as valence and stability permit,
W, $R^1$, $R^{12}$, $R^{13}$, $R^{14}$, $R^{15}$, and ring A are as defined for formulae (I) and (II), above; and further wherein:
$R^a$ represents optionally substituted alkyl, aryl, or alkoxyl; and
X represents a halide, carbonate, sulfonate, acetate, or carboxylate.

In certain embodiments, the compound of formula (I) is represented by formula (Ia):

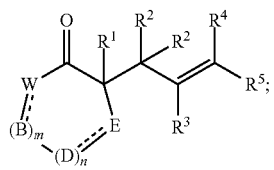

and
the compound of formula (IV) is represented by formula (IVa):

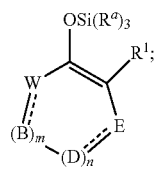

and
the compound of formula (V) is represented by formula (Va):

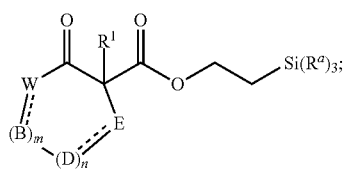

wherein substituents B, D, E, n, and m are defined above for formulae (Ia), (IIa), and (IIIa).

In certain embodiments, the alkylation conditions under which the compound of formula (IV) or (V) reacts to form a compound of formula (I) further comprise a fluoride source, such as TBAT, TBAF, $LiBF_4$, or a tetraalkylammonium fluoride salt.

In certain embodiments, the method for preparing a compound of formula (I) comprises treating a compound of formula (IV) with a Pd(II) catalyst under alkylation conditions.

In certain embodiments, the method for preparing a compound of formula (I) comprises treating a compound of formula (V) with a Pd(II) catalyst under alkylation conditions.

Transition Metal Catalysts

Preferred transition metal catalysts of the invention are complexes of palladium (II).

It should be appreciated that typical transition metal catalysts having a low oxidation state (e.g., (0) or (I)) suffer from air- and moisture-sensitivity, such that these complexes of transition metals necessitate appropriate handling precautions. This may include the following precautions without limitation: minimizing exposure of the reactants to air and water prior to reaction; maintaining an inert atmosphere within the reaction vessel; properly purifying all reagents; and removing water from reaction vessels prior to use.

Palladium (II) catalysts are typically robust, and are less sensitive to air and moisture than their lower-oxidation state counterparts.

Exemplary Pd (II) catalysts that may be used in the methods of the invention include $Pd(OC(O)R^c)_2$, wherein $R^c$ is optionally substituted alkyl, alkenyl, alkynyl, aryl, heteroaryl, aralkyl, heteroaralkyl, cycloalkyl, heterocycloalkyl, (cycloalkyl)alkyl, or (heterocycloalkyl)alkyl. Further exemplary Pd (II) catalysts include $Pd(OC(O)R^c)_2$, $Pd(OC(\!=\!O)CH_3)_2$ (i.e., $Pd(OAc)_2$), $Pd(TFA)_2$, $Pd(acac)_2$, $PdCl_2$, $PdBr_2$, $PdCl_2(R^{23}CN)_2$ (e.g., $Pd(PhCN)_2Cl_2$ and $Pd(CH_3CN)_2Cl_2$), $PdCl_2(PR^{24}R^{25}R^{26})_2$, $[Pd(\eta^3\text{-allyl})Cl]_2$, and pre-formed Pd(II)-ligand complex, wherein $R^{23}$, $R^{24}$, $R^{25}$, and $R^{26}$ are independently selected from hydrocarbyl, substituted hydrocarbyl, heteroatom-containing hydrocarbyl, and substituted heteroatom-containing hydrocarbyl. In preferred embodiments, the transition metal catalyst is $Pd(OAc)_2$. Alternatively, the transition metal catalyst is $Pd(OC(O)R^c)_2$, wherein $R^c$ is defined above. For example, $R^c$ may be alkyl, substituted by one or more halo or cyano groups.

To improve the effectiveness of the catalysts discussed herein, additional reagents may be employed, including, without limitation, salts, solvents, and other small molecules. Preferred additives include $AgBF_4$, $AgOSO_2CF_3$, $AgOC(\!=\!O)CH_3$, and bipyridine. These additives are preferably used in an amount that is in the range of about 1 equivalent to about 5 equivalents relative to the amount of the catalyst.

A low oxidation state of a transition metal, i.e., an oxidation state sufficiently low to undergo oxidative addition, can be obtained in situ, by the reduction of transition metal complexes that have a high oxidation state. Reduction of the transition metal complex can optionally be achieved by adding nucleophilic reagents including, without limitation, tetrabutylammonium hydroxide, tetrabutylammonium difluorotriphenylsilicate (TBAT), tetrabutylammonium fluoride (TBAF), 4-dimethylaminopyridine (DMAP), tetramethylammonium hydroxide (e.g., as the pentahydrate), KOH/ 1,4,7,10,13,16-hexaoxacyclooctadecane, sodium ethoxide, TBAT/trimethyl-(2-methyl-cyclohex-1-enyloxy)-silane, and combinations thereof. When a nucleophilic reagent is needed for the reduction of the metal complex, the nucleophilic reagent is used in an amount in the range of about 1 mol % to about 20 mol % relative to the reactant, more preferably in the range of about 1 mol % to about 10 mol % relative to the substrate, and most preferably in the range of about 5 mol % to about 8 mol % relative to the substrate.

For example, a Pd(II) complex can be reduced in situ to form a Pd(0) catalyst. Exemplary transition metal complexes that may be reduced in situ, include, without limitation, allylchloro[1,3-bis(2,6-di-iso-propylphenyl)imidazol-2-ylidene]palladium(II), ([2S,3S]-bis[diphenylphosphino]butane)($\eta^3$-allyl)palladium(II) perchlorate, [S]-4-tert-butyl-2-(2-diphenylphosphanyl-phenyl)-4,5-dihydro-oxazole($\eta^3$-allyl)palladium(II) hexafluorophosphate (i.e., [Pd(S-tBuPHOX)(allyl)]PF$_6$), and cyclopentadienyl($\eta^3$-allyl)palladium(II).

Accordingly, when describing the amount of transition metal catalyst used in the methods of the invention, the following terminology applies. The amount of transition metal catalyst present in a reaction is alternatively referred to herein as "catalyst loading". Catalyst loading may be expressed as a percentage that is calculated by dividing the moles of catalyst complex by the moles of the substrate present in a given reaction. Catalyst loading is alternatively expressed as a percentage that is calculated by dividing the moles of total transition metal (for example, palladium) by the moles of the substrate present in a given reaction.

In certain embodiments, the transition metal catalyst is present under the conditions of the reaction from an amount of about 0.01 mol % to about 10 mol % total palladium relative to the substrate, which is the compound of formula (II), (III), (IV), or (V). In certain embodiments, the catalyst loading is from about 0.05 mol % to about 5 mol % total palladium relative to the substrate. In certain embodiments, the catalyst loading is from about 0.05 mol % to about 2.5 mol %, about 0.05 mol % to about 2%, about 0.05 mol % to about 1%, about 0.02 mol % to about 5 mol %, about 0.02 mol % to about 2.5 mol %, about 0.02 mol % to about 1 mol %, about 0.1 mol % to about 5 mol %, about 0.1 mol % to about 2.5 mol %, or about 0.1 mol % to about 1 mol % total palladium relative to the substrate. For example, in certain embodiments, the catalyst loading is about 0.01 mol %, about 0.05 mol %, about 0.1 mol %, about 0.15 mol %, about 0.2 mol %, about 0.25 mol %, about 0.3 mol %, about 0.4 mol %, about 0.5 mol %, about 0.6 mol %, about 0.7 mol %, about 0.8 mol %, about 0.9 mol %, about 1 mol %, about 1.5 mol %, about 2 mol %, about 3 mol %, or about 5 mol % total palladium.

Ligands

One aspect of the invention relates to the enantioselectivity of the methods. Enantioselectivity results from the use of chiral ligands during the allylic alkylation reaction. Accordingly, in certain embodiments, the Pd (II) catalyst further comprises a chiral ligand. Without being bound by theory, the asymmetric environment that is created around the metal center by the presence of chiral ligands produces an enantioselective reaction. The chiral ligand forms a complex with the transition metal (i.e., palladium), thereby occupying one or more of the coordination sites on the metal and creating an asymmetric environment around the metal center. This complexation may or may not involve the displacement of achiral ligands already complexed to the metal. When displacement of one or more achiral ligands occurs, the displacement may proceed in a concerted fashion, i.e., with both the achiral ligand decomplexing from the metal and the chiral ligand complexing to the metal in a single step. Alternatively, the displacement may proceed in a stepwise fashion, i.e., with decomplexing of the achiral ligand and complexing of the chiral ligand occurring in distinct steps. Complexation of the chiral ligand to the transition metal may be allowed to occur in situ, i.e., by admixing the ligand and metal before adding the substrate. Alternatively, the ligand-metal complex can be formed separately, and the complex isolated before use in the alkylation reactions of the present invention.

Once coordinated to the transition metal center, the chiral ligand influences the orientation of other molecules as they interact with the transition metal catalyst. Coordination of the metal center with a π-allyl group and reaction of the substrate with the π-allyl-metal complex are dictated by the presence of the chiral ligand. The orientation of the reacting species determines the stereochemistry of the products.

Chiral ligands of the invention may be bidentate or monodentate or, alternatively, ligands with higher denticity (e.g., tridentate, tetradentate, etc.) can be used. Preferably, the ligand will be substantially enantiopure. By "enantiopure" is meant that only a single enantiomer is present. In many cases, substantially enantiopure ligands (e.g., ee >99%, preferably >99.5%, even more preferably >99.9%) can be purchased from commercial sources, obtained by successive recrystallizations of an enantioenriched substance, or by other suitable means for separating enantiomers.

Exemplary chiral ligands may be found in U.S. Pat. No. 7,235,698, the entirety of which is incorporated herein by reference. In certain embodiments, the chiral ligand is an enantioenriched phosphine ligand. In certain embodiments, the enantioenriched phosphine ligand is a P,N-ligand such as a phosphinooxazoline (PHOX) ligand. Preferred chiral ligands of the invention include the PHOX-type chiral ligands such as (R)-2-[2-(diphenylphosphino)phenyl]-4-isopropyl-2-oxazoline, (R)-2-[2-(diphenylphosphino)phenyl]-4-phenyl-2-oxazoline, (S)-2-[2-(diphenylphosphino)phenyl]-4-benzyl-2-oxazoline, (S)-2-[2-(diphenylphosphino)phenyl]-4-tert-butyl-2-oxazoline ((S)-t-BuPHOX) and (S)-2-(2-(bis(4-(Trifluoromethyl)phenyl)phosphino)-5-(trifluoromethyl)phenyl)-4-(tert-butyl)-4,5-dihydrooxazole ((S)—(CF$_3$)$_3$-t-BuPHOX). In preferred embodiments, the PHOX type chiral ligand is selected from (S)-t-BuPHOX and (S)—(CF$_3$)$_3$-t-BuPHOX). The ligand structures are depicted below.

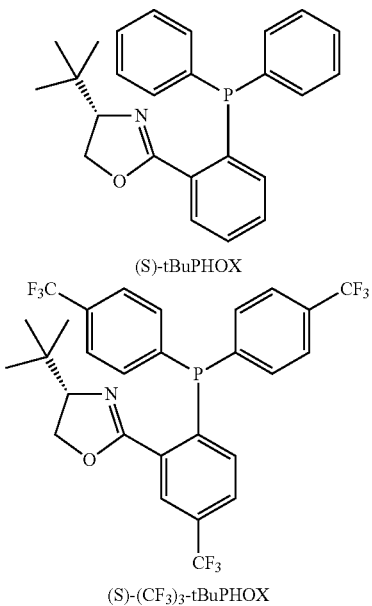

Generally, the chiral ligand is present in an amount in the range of about 1 equivalents to about 20 equivalents relative to the amount of total metal from the catalyst, preferably in the range of about 5 to about 15 equivalents relative to the amount of total metal from the catalyst, and most preferably in the range of about 10 equivalents relative to the amount of total metal from the catalyst. Alternatively, the amount of the chiral ligand can be measured relative to the amount of the substrate.

In certain embodiments, the ligand is present under the conditions of the reaction from an amount of about 0.1 mol % to about 100 mol % relative to the substrate, which is the compound of formula (II), (III), (IV), or (V). The amount of ligand present in the reaction is alternatively referred to herein as "ligand loading" and is expressed as a percentage that is calculated by dividing the moles of ligand by the moles of the substrate present in a given reaction. In certain embodiments, the ligand loading is from about 0.5 mol % to about 50 mol %. For example, in certain embodiments, the ligand loading is about about 1 mol %, about 1.5 mol %, about 2 mol %, about 2.5 mol %, about 3 mol %, about 4 mol %, or about 5 mol %. In certain embodiments, the ligand is in excess of the transition metal catalyst. In certain embodiments, the ligand loading is about 10 times the transition metal catalyst loading. Without being bound to theory, it is thought that the ligand (e.g., the PHOX ligand) may act as the reductive agent that generates Pd(0) in situ.

Where a chiral ligand is used, the reactions of the invention may enrich the stereocenter bearing $R^1$ in the product relative to the enrichment at this center, if any, of the starting material. In certain embodiments, the chiral ligand used in the methods of the invention yields a compound of formula (I) that is enantioenriched. The level of enantioenrichment of a compound may be expressed as enantiomeric excess (ee). The ee of a compound may be measured by dividing the difference in the fractions of the enantiomers by the sum of the fractions of the enantiomers. For example, if a compound is found to comprise 98% (S)-enantiomer, and 2% (R) enantiomer, then the ee of the compound is (98−2)/(98+2), or 96%. In certain embodiments, the compound of formula (I) has about 30% ee or greater, 40% ee or greater, 50% ee or greater, 60% ee or greater, 70% ee or greater, about 80% ee, about 85% ee, about 88% ee, about 90% ee, about 91% ee, about 92% ee, about 93% ee, about 94% ee, about 95% ee, about 96% ee, about 97% ee, about 98% ee, about 99% ee, or above about 99% ee, even where this % ee is greater than the % ee of the starting material, such as 0% ee (racemic). In certain embodiments, the compound of formula (I) is enantioenriched. In certain embodiments, the compound of formula (I) is enantiopure. In embodiments where the starting material has more than one stereocenter, reactions of the invention may enrich the stereocenter bearing $R^1$ relative to the enrichment at this center, if any, of the starting material, and substantially independently of the stereochemical disposition/enrichment of any other stereocenters of the molecule. For example, a product of the methods described herein may have 30% de or greater, 40% de or greater, 50% de or greater, 60% de or greater, 70% de or greater, 80% de or greater, 90% de or greater, 95% de or greater, or even 98% de or greater at the stereocenter of the product bearing $R^1$.

In certain embodiments, the invention also relates to methods that utilize an achiral ligand. Exemplary achiral ligands include triphenylphosphine, tricyclohexylphosphine, tri-(ortho-tolyl)phosphine, trimethylphosphite, and triphenylphosphite.

Alkylation Conditions

In certain embodiments, the methods of the invention include treating a compound of formula (II), (III), (IV), or (V) with a Pd (II) catalyst under alkylation conditions. In certain embodiments, alkylation conditions of the reaction include one or more organic solvents. In certain embodiments, organic solvents include aromatic or non-aromatic hydrocarbons, ethers, alkylacetates, nitriles, or combinations thereof. In certain embodiments, organic solvents include hexane, pentane, benzene, toluene, xylene, cyclic ethers such as optionally substituted tetrahydrofuran and dioxane, acyclic ethers such as dimethoxyethane, diethyl ether, methyl tertbutyl ether, and cyclopentyl methyl ether, acetonitrile, isobutyl acetate, ethyl acetate, isopropyl acetate, or combinations thereof. In certain preferred embodiments, the solvent is toluene, methyl tertbutyl ether, or 2-methyltetrahydrofuran. In certain other preferred embodiments, the solvent is methyl tertbutyl ether.

In certain embodiments, alkylation conditions of the reaction include a reaction temperature. In certain embodiments, the reaction temperature is ambient temperature (about 20° C. to about 26° C.). In certain embodiments, the reaction temperature is higher than ambient temperature, such as, for example, about 30° C., about 35° C., about 40° C., about 45° C., about 50° C., about 55° C., or about 60° C. Reaction temperature may be optimized per each substrate.

In certain embodiments, instruments such as a microwave reactor may be used to accelerate the reaction time. Pressures range from atmospheric to pressures typically used in conjunction with supercritical fluids, with the preferred pressure being atmospheric.

EXEMPLIFICATION

The invention described generally herein will be more readily understood by reference to the following examples, which are included merely for purposes of illustration of certain aspects and embodiments of the present invention, and are not intended to limit the invention.

Example 1

Exploration of Alternative Pd-catalyst $Pd_2(dba)_3$ is known to be oxygen-sensitive. In order to increase the scalability of the reaction, alternative Pd-based catalysts were explored. The catalytic cycle of the allylic alkylation operates starting from a zero valent palladium source and is believed to involve a palladium (0/II) redox cycle.[6] While utilization of $Pd_2(dba)_3$ renders in situ reduction of the catalyst obsolete, its application is hampered by increased sensitivity to oxygen. Furthermore, the dibenzylideneacetone ligand is challenging to separate from nonpolar reaction products. Below is a survey of a variety of Pd(II) sources in combination with the chiral phosphinooxazoline ligands (S)-t-BuPHOX 3 [7] and (S)—(CF_3)_3-t-BuPHOX 4.[8]

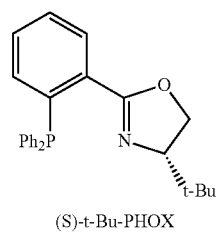

(S)-t-Bu-PHOX

-continued

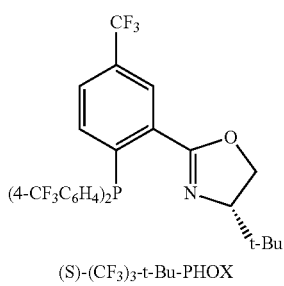

(S)-(CF$_3$)$_3$-t-Bu-PHOX

TABLE 1

Comparison between palladium precursors in different oxidation states.

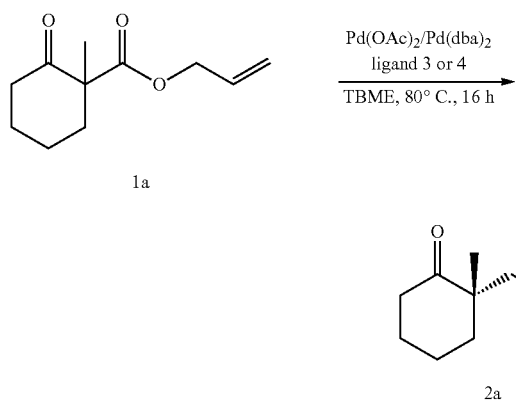

| Entry | Ligand [mmol] | Pd source | [mol %] Pd | Yield [%] a) | ee [%] b) |
|---|---|---|---|---|---|
| 1 | 3  10.0 | Pd(OAc)$_2$ | 1.0 | 99 | 86 |
| 2 | 4  10.0 | Pd(OAc)$_2$ | 1.0 | 99 | 82 |
| 3 | 3  10.0 | Pd$_2$(dba)$_3$ | 1.0 | 99 | 84 |
| 4 | 4  10.0 | Pd$_2$(dba)$_3$ | 1.0 | 90 | 82 |
| 5 | 3  1.0 | Pd(OAc)$_2$ | 0.1 | 99 | 79 |
| 6 | 4  1.0 | Pd(OAc)$_2$ | 0.1 | 99 | 83 |
| 7 | 3  1.0 | Pd$_2$(dba)$_3$ | 0.1 | 12 | n.d. |
| 8 | 4  1.0 | Pd$_2$(dba)$_3$ | 0.1 | 14 | n.d. | a) GC yield relative to an internal standard (tridecane).
b) Enantiomeric excess measured by chiral GC.

When comparing Pd(OAc)$_2$ and Pd$_2$(dba)$_3$ at 1.0 mol % palladium in combination with a tenfold excess of PHOX ligands 3 or 4 respectively, in TBME at 80° C. both palladium sources exhibited comparable catalytic performance (Table 1, entries 1-4). At lower palladium concentrations, however, Pd(OAc)$_2$ was clearly superior, delivering quantitative yields and good enantioselectivity at only 0.10 mol % Pd (Table 1, entries 5 and 6). When 0.10 mol % Pd$_2$(dba)$_3$ was used to form the catalyst, a dramatic decrease in yields was observed (Table 1, entries 7 and 8).

Other palladium(II) sources were then investigated to determine whether the sources were equally suited to catalyze the decarboxylative allylic alkylation. Consequently, a total of eight different commercially available Pd(II) precursors were examined in our model reaction in the presence of ligand 3 (Pd(OAc)$_2$, PdCl$_2$, Pd(PhCN)$_2$Cl$_2$, Pd(CH$_3$CN)$_2$Cl$_2$, PdBr$_2$, Pd(acac)$_2$, [Pd(allyl)Cl]$_2$, Pd(TFA)$_2$). Solubility of certain palladium salts in TBME can hinder catalysis.

Example 2

Exploration of Catalyst Loading

Using Pd(OAc)$_2$ as the palladium catalyst precursor, we turned our attention to minimizing the catalyst loading. A screening of six different catalyst loadings, ranging from 0.05 mol % to 1.0 mol %, was performed (Table 2). All reactions were conducted in the presence of a tenfold excess of ligand with respect to palladium, in TBME at 40° C. The high-excess of ligand was chosen to facilitate formation of the active catalyst through in situ reduction of Pd(OAc)$_2$. We reasoned that the PHOX ligand hereby acts as the reductive agent.

Under these reaction conditions, palladium loadings as low as 0.10 mol % were sufficient to deliver the desired allylic alkylation product in 90% yield and with high enantioselectivity (Table 2, entry 5). To obtain a quantitative yield of ketone 2a, the catalyst loading was increased to 0.15 mol % of Pd(OAc)$_2$ (Table 2, entry 4).

TABLE 2

Assessment of the Pd(OAc)$_2$ loading for the decarboxylative allylic alkylation.

| Entry | Pd [mol %] | 3 [mol %] | Yield [%] a) | ee [%] b) |
|---|---|---|---|---|
| 1 | 1.00 | 10.0 | 99 | 90 |
| 2 | 0.50 | 5.0 | 99 | 90 |
| 3 | 0.25 | 2.50 | 99 | 90 |
| 4 | 0.15 | 1.50 | 99 | 89 |
| 5 | 0.10 | 1.0 | 90 | 89 |
| 6 | 0.05 | 0.50 | 10 | 89 | a) GC yield relative to an internal standard (tridecane).
b) Enantiomeric excess measured by chiral GC.

Example 3

Solvent Survey

Enantioselective allylic alkylation reactions are typically performed in solvents such as THF, DCM, dioxane, or diethylether. While these solvents are common for academic laboratory scale, their use prohibits conducting the reaction in an industrial setting. We sought to overcome this limitation and performed a solvent survey with a total of ten different solvents that are considered to be safe, sustainable and cost-efficient (Table 3).[9,10]

Conversion of allyl 1-methyl-2-oxocyclohexane-carboxylate (1a) in TBME resulted in a high yield and good enantioselectivity (Table 3, entry 1). When the reaction was performed in various alkyl acetates the yields dropped dramatically, to 12%, 28% and 17% respectively (Table 3, entries 2, 4 and 5). Similarly low yields were observed for reactions performed in acetonitrile, dimethylacetamide, 2-Me-THF, and acetone (Table 3, entries 3, 6, 8 and 10). Moderate conversion was found when the reaction was performed in toluene (Table 3, entry 7). Consequently, all further experiments were carried out in TBME.

TABLE 3

Assessment of the reaction medium.

| Entry | solvent | Yield [%] [a] | ee [%] [b] |
|---|---|---|---|
| 1 | TBME | 88 | 89 |
| 2 | EtOAc | 12 [c] | 74 |
| 3 | Acetonitrile | trace | — |
| 4 | Isopropyl acetate | 28 | 64 |
| 5 | Isobutyl acetate | 17 | — |
| 6 | Dimethylacetamide | trace | — |
| 7 | Toluene | 52 | 80 |
| 8 | 2-Me-THF | 21 | 89 |
| 9 | t-AmylOH | — [c] | — |
| 10 | Acetone | 12 [c] | 47 |

[a] GC yield relative to an internal standard (tridecane).
[b] Enantiomeric excess measured by chiral GC.
[c] Reaction performed at 60° C.

Example 4

Temperature Survey

At this point, we considered that the palladium concentration could be lowered further by performing the reaction at higher temperatures, and we were interested in the influence of increased reaction temperature on stereoselectivity. All experiments were performed in TBME with a tenfold excess of ligand 3 (Table 4). A palladium loading as low as 0.075 mol % afforded ketone 2a in 99% yield when the reaction was performed at 80° C., which corresponds to a turnover number of 1320 for the in situ formed catalyst. Nevertheless, a slightly lower enantioselectivity of 84% was observed in this case (Table 4, entry 1). At 60° C. and 40° C., palladium loadings of 0.10 and 0.125 mol % respectively were sufficient to deliver the desired product in quantitative yield and retain high enantioselectivity (Table 4, entries 2 and 3).

TABLE 4

Assessment of the palladium loading for the decarboxylative allylic alkylation at various temperatures.

| Entry | Pd [mol %] | T [° C.] | Yield [%] [a] | ee [%] [b] |
|---|---|---|---|---|
| 1 | 0.075 | 80 | 99 | 84 |
| 2 | 0.10 | 60 | 99 | 88 |
| 3 | 0.125 | 40 | 99 | 89 |

[a] GC yield relative to an internal standard (tridecane).
[b] Enantiomeric excess measured by chiral GC.

Example 5

Increasing Reaction Scale

We then applied the protocol to the 10 and 20 mmol scale synthesis of alpha-quaternary ketones 2a and 2b (Table 5). Both reactions were performed in TBME with a tenfold excess of ligand 3. Cyclohexanone 1a was converted on a 10.0 mmol scale (1.96 g) in the presence of 0.15 mol (3.37 mg) of Pd(OAc)$_2$ at 60° C. The corresponding product 2a was isolated by distillation in excellent yield and high enantioselectivity (Table 5, entry 1). Similarly, tetralone substrate 1b was subjected to enantioselective allylic alkylation conditions at 40° C. on a 20 mmol scale (4.89 g). The desired product 2b was purified by flash chromatography and isolated in 95% yield and 88% ee (Table 5, entry 2).

TABLE 5

Scale-up experiments.

TABLE 5-continued

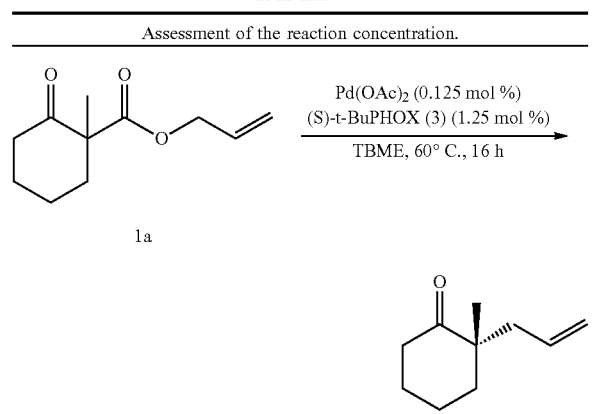

| Entry | Substrate | Scale [mol] | T [° C.] | Pd [mol %] | Yield [%] | ee [%] |
|---|---|---|---|---|---|---|
| 1 | Cyclohexanone 1a | 0.01 | 60 | 0.150 | 95 [a] | 89 [c] |
| 2 | Tetralone 1b | 0.02 | 40 | 0.125 | 95 [b] | 88 [d] |

[a] Isolated yield, purification by distillation.
[b] Isolated yield, purification by flash chromatography.
[c] Enantiomeric excess measured by chiral GC.
[d] Enantiomeric excess measured by chiral SFC.

Example 6

Ligand Loading and Reaction Concentration

Six experiments were conducted, employing different quantities of ligand, from 0.20 mol % to 1.0 mol %, in the presence of 0.10 mol % Pd(OAc)$_2$ (Table 6). A ligand loading of 0.40 mol %, which corresponds to a 4-fold excess of ligand with respect to palladium, was sufficient to provide the desired product in quantitative yield and high enantioselectivity (Table 6, entry 4). Only at a loading of 0.20 mol % of ligand 3 a slight decrease in enantioselectivity was observed (Table 6, entry 5).

TABLE 6

Assessment of the ligand loading for the decarboxylative allylic alkylation.

| Entry | Ligand 3 [mol %] | Yield [%] [a] | ee [%] [b] |
|---|---|---|---|
| 1 | 1.00 | 99 | 88 |
| 2 | 0.80 | 99 | 89 |
| 3 | 0.60 | 99 | 88 |
| 4 | 0.40 | 99 | 88 |
| 5 | 0.20 | 99 | 86 |

[a] GC yield relative to an internal standard (tridecane).
[b] Enantiomeric excess measured by chiral GC.

Finally, we investigated the influence of concentration on reactivity. A brief study across five different substrate concentrations was executed (Table 7).

TABLE 7

Assessment of the reaction concentration.

| Entry | concentration [M] | Yield [%] [a] | ee [%] [b] |
|---|---|---|---|
| 1 | 0.40 | 99 | 88 |
| 2 | 0.20 | 99 | 88 |
| 3 | 0.10 | 99 | 89 |
| 4 | 0.05 | 99 | 89 |
| 5 | 0.033 | 91 | 87 |

[a] GC yield relative to an internal standard (tridecane).
[b] Enantiomeric excess measured by chiral GC.

We were pleased to find that the decarboxylative alkylation reaction could be performed in high concentrations of up to 0.40 M without any negative impact on yield or enantiomeric excess (Table 7, entry 1). When the reaction was performed at higher dilution (0.033 M) a slight decrease in yield and optical purity was observed (Table 7, entry 5).

Example 7

Lactams as Substrates

The decarboxylative allylic alkylation of lactams is particularly useful and important, given the prevalence of quaternary N-heterocyclesin biologically active alkaloids and their potential importance in pharmaceutical agents.[11] Initial experiments suggested that higher palladium loadings were required for the decarboxylative allylic alkylation of piperidinones. Consequently, a brief study was performed to determine the minimal palladium loading needed to efficiently catalyze the reaction (Table 8). The electron-poor ligand (S)—(CF$_3$)$_3$-t-BuPHOX 4 was applied in the presence of varying amounts of Pd(OAc)$_2$ in TBME at 60° C.

TABLE 8

Assessment of the palladium loading for the decarboxylative allylic alkylation of lactams.

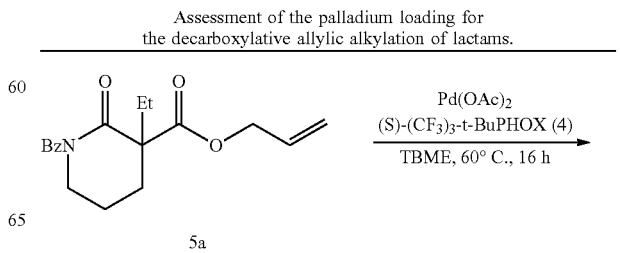

TABLE 8-continued

![Structure 6a: piperidinone with BzN, Et, and allyl substituents]

6a

| Entry | Pd [mol %] | 4 [mol %] | Yield [%] [a] | ee [%] [b] |
|---|---|---|---|---|
| 1 | 0.50 | 5.0 | 87 | 96 |
| 2 | 0.30 | 3.0 | 85 | 97 |
| 3 | 0.10 | 1.0 | 77 | 84 |

[a] GC yield relative to an internal standard (tridecane).
[b] Enantiomeric excess measured by HPLC.

At 0.10 mol % of $Pd(OAc)_2$ the desired product was obtained in only 77% yield and a reduced enantioselectivity of 84% ee. (Table 8, entry 3) Nevertheless, a catalyst concentration of only 0.30 mol % was sufficient to render the chiral lactam 6a in 85% yield and 97% ee (Table 8, entry 2). Compared to the original report, in which 5.0 mol % of $Pd_2(dba)_3$ were applied, this constitutes a more than thirty-fold decrease in palladium loading.

Example 8

Additional Substrate Studies

To demonstrate the broad applicability of this novel protocol, a total of ten compounds were subjected to the improved reaction parameters (Table 9). Asymmetric allylic alkylation to generate products 2a, 2b and 6a was discussed previously in detail (Table 9, entries 1-3). Allylmethylpiperidinone 6b and allylfluoropiperidinone 6d were synthesized in a similar fashion. Yields of 81% and 80% respectively, and enantioselectivities of up to 99% could be obtained (Table 9, entry 4 and 6). In the latter case, a catalyst loading as low as 0.125 mol % was sufficient to yield the product in near to perfect enantioselectivity. Despite the 80-fold reduction in palladium loading compared to the original procedure, no erosion of enantioselectivity was observed (Table 9, entry 6).

Gratifyingly, the novel allylic alkylation protocol could be applied to seven-membered rings as well; however, despite a near quantitative yield only reduced enantiomeric excess of 70% was observed for ketone 2c (Table 9, entry 7). Nevertheless, seven-membered caprolactam 6e was isolated in 95% yield and high enantioselectivity (Table 9, entry 8). Notably, despite the dilution, cyclohexylketal 2d was generated in 79% yield and good enantioselectivity through intermolecular allylic alkylation of the corresponding silyl enol ether and allyl methanesulfonate (Table 9, entry 9).

Finally, cyclohexanedione 2e, which is a critical intermediate in the synthesis of (−)-cyanthiwigin F,[12] could be accessed through double enantioselective allylic alkylation of the bis(□-ketoester) 1e in excellent yield and near perfect enantioselectivity using only 0.25 mol % palladium. This corresponds to 5% of the palladium loading used in the original protocol. Despite the considerable reduction in catalyst concentration the yield for this reaction was improved to 97% (Table 9, entry 10).

TABLE 9

Scope of the decarboxylative allylic alkylation. [a]

| Entry | Product | Protocol | Pd [mol %] | Yield [%] | ee [%] |
|---|---|---|---|---|---|
| 1 | ![2a structure: allyl methyl cyclohexanone] 2a | old<br>new | 5.00<br>0.125 | 89<br>99 [b] | 88<br>89 |
| 2 | ![2b structure: allyl methyl tetralone] 2b | old<br>new | 8.00<br>0.125 | 97<br>85 [b] | 92<br>89 |
| 3 | ![6a structure: BzN piperidinone with Et and allyl] 6a | old<br>new | 10.0<br>0.30 | 97<br>85 [f] | 99<br>97 |

TABLE 9-continued

Scope of the decarboxylative allylic alkylation.[a]

| Entry | Product | Protocol | Pd [mol %] | Yield [%] | ee [%] |
|---|---|---|---|---|---|
| 4 | 6b | old<br>new | 10.0<br>0.50 | 85<br>81 [f] | 99<br>95 |
| 5 | 6c | old<br>new | 10.0<br>0.125 | 91<br>99 [f] | 94<br>88 |
| 6 | 6d | old<br>new | 10.0<br>0.125 | 89<br>80 [f] | 99<br>99 |
| 7 | 2c | old<br>new | 5.00<br>0.10 | 83<br>97 [e],[f] | 87<br>70 |
| 8 | 6e (R = p-OMe—C$_6$H$_4$) | old<br>new | 5.00<br>0.125 | 83<br>95 [f] | 93<br>90 |
| 9 | 6b | old<br>new | —<br>0.10 | —<br>79 [c],[e],[f] | —<br>90 |

TABLE 9-continued

Scope of the decarboxylative allylic alkylation.[a]

| Entry | Product | Protocol | Pd [mol %] | Yield [%] | ee [%] |
|---|---|---|---|---|---|
| 10 | 2e | old<br>new | 5.00<br>0.25 | 78<br>97 [d),e),f),h)] | 99<br>99 [g)] |

[a)] Conditions: Reactions were performed according to the "general procedure" in TBME at 60° C. with a tenfold excess of ligand 3 with respect to Pd.
[b)] Temperature: 40° C.
[c)] Temperature: 32° C.
[d)] Temperature: 27° C.
[e)] Reaction performed in toluene.
[f)] Ligand 4 was used.
[g)] Diketone 2e was obtained in 4.85:1.00 d.r.
[h)] Isolated yield. GC yield relative to an internal standard (tridecane).
Enantiomeric excess measured by chiral GC, HPLC or SFC.

Example 9

Experimental Procedures

Low Pd-Loading Allylic Alkylation Reactions—General Method

In a nitrogen-filled glove box, Pd(OAc)$_2$ (1.1 mg, 4.9 µmol) was weighed into a 20 mL scintillation vial and dissolved in TBME (20 mL). In a separate 1-dram vial, (S)-t-BuPHOX (1.9 mg, 4.9 µmol) was dissolved in TBME (1 mL). To a 2-dram vial equipped with a magnetic stirbar, 1.02 mL of the Pd(OAc)$_2$ solution was added (56 µg, 0.25 µmol, 0.125 mol %) followed by 0.51 mL of the (S)-t-BuPHOX solution (0.97 mg, 2.5 µmol, 1.25 mol %). This mixture was stirred at ambient temperature (28° C.) in the glove box for 30-40 min. Substrate (0.20 mmol, 1.0 equiv) was taken up in TBME (0.5 mL) and added to the stirring catalyst solution. For reactions analyzed by GC, tridecane (24 µL, 0.1 mmol, 0.5 equiv) was added. The reaction was sealed with a Teflon-lined cap, removed from the glove box and stirred at the indicated temperature for the indicated period of time. At this point, the reaction was analyzed by GC, or passed through a silica plug, concentrated in vacuo, and purified by column chromatography.

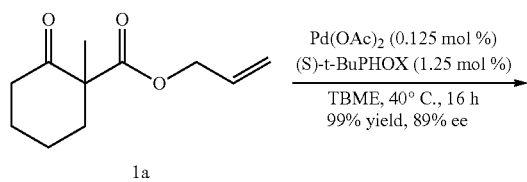

1a

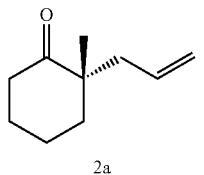

2a (S)-2-allyl-2-methylcyclohexan-1-one (2a). Synthesized according to the general method from cyclohexanone 1a. The reaction was passed through a plug of SiO$_2$ and analyzed by GC (99% yield). The product could be isolated by column chromatography (SiO$_2$, 5% Et$_2$O in pentane) as a colorless oil and matched previously reported characterization data.

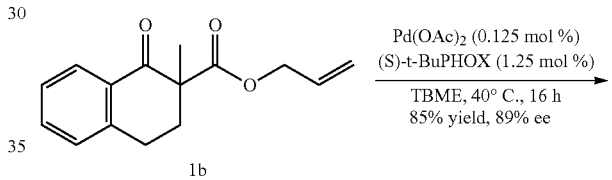

1b

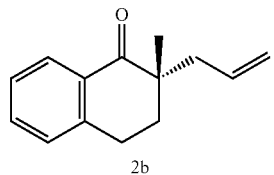

2b (S)-2-allyl-2-methyl-3,4-dihydronaphthalen-1(2H)-one (2b). Synthesized according to the general method from tetralone 1b. Product was isolated by column chromatography (SiO$_2$, 5-10% Et$_2$O in hexanes) as a pale yellow oil (85% yield) and matched previously reported characterization data.

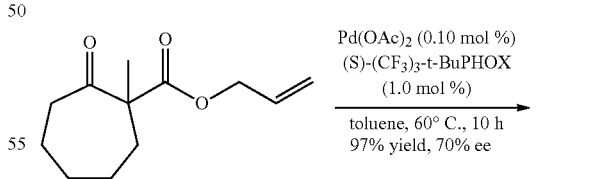

1c

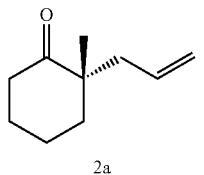

2c (S)-2-allyl-2-methylcycloheptan-1-one (2c). Synthesized according to the general method from cycloheptanone 1c using 1.0 mol % (S)-t-BuPHOX and 0.10 mol % Pd(OAc)$_2$ in toluene at 60° C. for 10 h. Product was isolated by column chromatography (SiO$_2$, 3% Et$_2$O in pentane) as a colorless oil (97% yield) and matched previously reported characterization data.

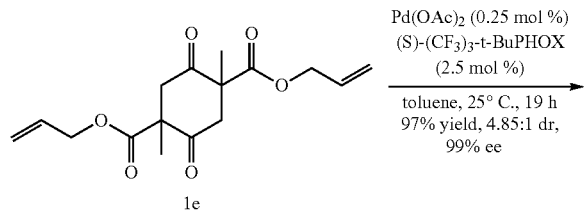

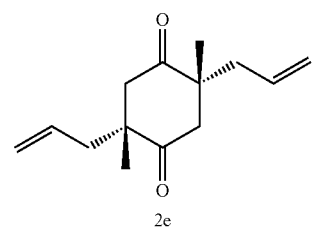

(2R,5R)-2,5-diallyl-2,5-dimethylcyclohexane-1,4-dione (2e). Synthesized according to the general method from diketone 1e using 2.5 mol % (S)—(CF$_3$)$_3$-t-BuPHOX and 0.25 mol % Pd(OAc)$_2$ in toluene at 25° C. for 19 h. Product was isolated by column chromatography (SiO$_2$, 3% EtOAc in hexanes) as a colorless oil (97% yield) and matched previously reported characterization data.

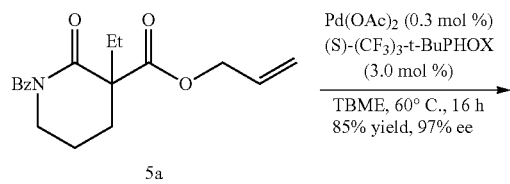

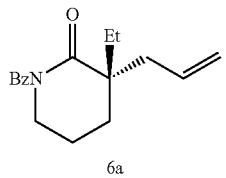

(S)-3-allyl-1-benzoyl-3-ethylpiperidin-2-one (6a). Synthesized according to the general method from lactam 5a using 3.0 mol % (S)—(CF$_3$)$_3$-t-BuPHOX and 0.30 mol % Pd(OAc)$_2$. Product was isolated by column chromatography (SiO$_2$, 15-20% Et$_2$O in hexanes) as a colorless oil (85% yield) and matched previously reported characterization data.

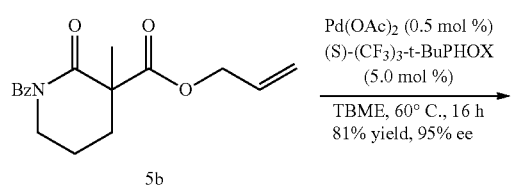

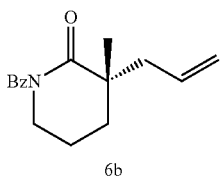

(S)-3-allyl-1-benzoyl-3-methylpiperidin-2-one (6b). Synthesized according to the general method from lactam 5b using 5.0 mol % (S)—(CF$_3$)$_3$-t-BuPHOX and 0.50 mol % Pd(OAc)$_2$. Product was isolated by column chromatography (SiO$_2$, 5-10% Et$_2$O in hexanes) as a colorless oil (81% yield) and matched previously reported characterization data.

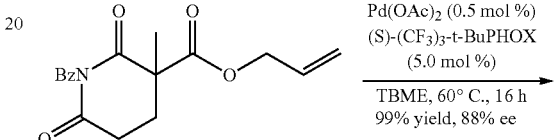

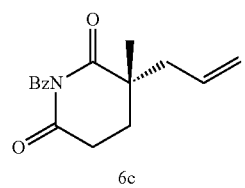

(S)-3-allyl-1-benzoyl-3-methylpiperidine-2,6-dione (6c). Synthesized according to the general method from imide 5c using 1.25 mol % (S)—(CF$_3$)$_3$-t-BuPHOX and 0.125 mol % Pd(OAc)$_2$. Product was isolated by column chromatography (SiO$_2$, 10-20% EtOAc in hexanes) as a colorless oil (99% yield) and matched previously reported characterization data.

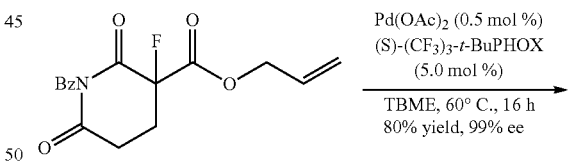

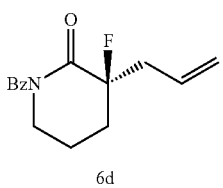

(R)-3-allyl-1-benzoyl-3-fluoropiperidin-2-one (6d). Synthesized according to the general method from lactam 5d using 1.25 mol % (S)—(CF$_3$)$_3$-t-BuPHOX and 0.125 mol % Pd(OAc)$_2$. Product was isolated by column chromatography (SiO$_2$, 10-20% EtOAc in hexanes) as a colorless oil (80% yield) and matched previously reported characterization data.

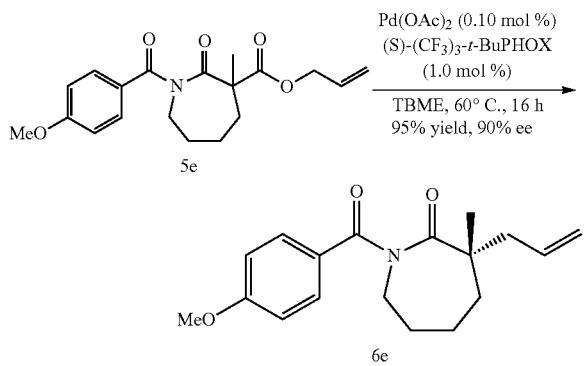

(S)-3-allyl-1-(4-methoxybenzoyl)-3-methylazepan-2-one (6e). Synthesized according to the general method from lactam 5e using 1.25 mol % (S)—(CF$_3$)$_3$-t-BuPHOX and 0.125 mol % Pd(OAc)$_2$. Product was isolated by column chromatography (SiO$_2$, 10-20% EtOAc in hexanes) as a colorless oil (95% yield) and matched previously reported characterization data.

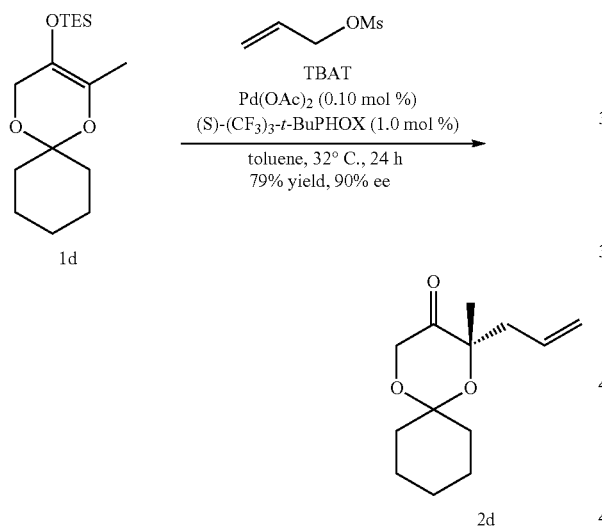

(S)-2-allyl-2-methyl-1,5-dioxaspiro[5.5]undecan-3-one (2d). A 20 mL vial was soaked in a 20:1 isopropanol:toluene bath saturated with potassium hydroxide for 12 h, rinsed with deionized water, acetone, and dried in a 120° C. oven overnight. The hot vial was the cycled into a nitrogen-filled glovebox and allowed to cool to ambient temperature. The vial was then charged Bu$_4$NPh$_3$SiF$_2$ (TBAT, 184 mg, 0.34 mmol, 1.00 equiv) and toluene (12.0 mL, 0.033 M) with stirring, followed by Pd(OAc)$_2$ (0.10 mg, 0.0004 mmol, 1.0 mg/mL in toluene, 0.00125 equiv) and (S)—(CF$_3$)$_3$-t-Bu-PHOX (2.37 mg, 0.004 mmol, 10 mg/mL in toluene, 0.0125 equiv). The reaction vessel was immediately introduced to a heat block at 32° C. and allowed to stir for 20 minutes. To the resulting tan solution was added allylmesylate (57 mg, 0.42 mmol, 1.20 equiv) quickly dropwise. After 3 minutes, silyl enol ether 1d (100 mg, 0.34 mmol, 1.00 equiv) was added quickly dropwise. Upon complete consumption of the enol ether (as determined by TLC analysis, 24 h), the resultant tan solution was removed from the heat block, allowed to cool to ambient temperature, and removed from the glove box. The reaction mixture was filtered through a pad of SiO$_2$ using hexanes eluent to remove toluene, followed by Et$_2$O eluent to isolate the volatile reaction products. The filtrate was concentrated in vacuo to a brown oil which was subsequently purified by flash chromatography (SiO$_2$, 4% Et$_2$O in hexanes) to afford volatile allyl ketal 2d (60 mg, 79% yield) as a clear, colorless oil: R$_f$=0.35 (19:1 hexanes:Et$_2$O); $^1$H NMR (400 MHz, CDCl$_3$), 5.85 (ddt, J=17.4, 10.3, 7.2 Hz, 1H), 5.14-5.03 (m, 2H), 4.20 (d, J=1.0 Hz, 2H), 2.51 (ddt, J=14.0, 7.2, 1.2 Hz, 1H), 2.41 (ddt, J=14.0, 7.2, 1.2 Hz, 1H), 1.87-1.42 (m, 10H), 1.38 (s, 3H); $^{13}$C NMR (101 MHz, CDCl$_3$), 211.4, 132.7, 118.8, 100.0, 82.0, 66.6, 44.0, 35.8, 35.5, 25.4, 24.7, 23.1, 23.1; IR (Neat Film, NaCl) 2938, 2860, 1742, 1446, 1365, 1259, 1159, 1112, 1056, 1000, 943, 916, 826 cm$^{-1}$; HRMS (EI+) m/z calc'd for C$_{13}$H$_{20}$O$_3$ [M•]$^+$: 224.1412, found 224.1409; [α]$_D^{25.0}$ −45.9° (c 1.10, CHCl$_3$, 90% ee).

Scale Up Procedures

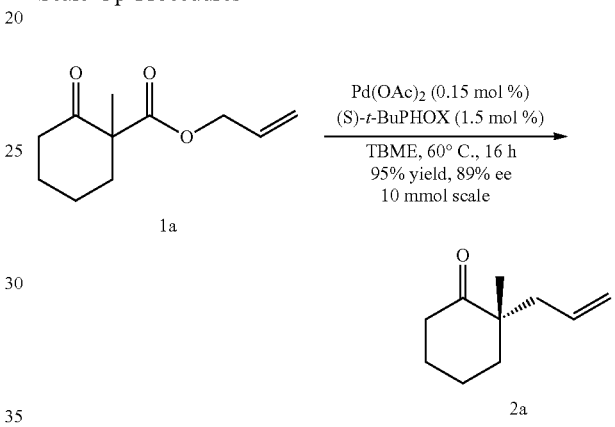

(S)-2-allyl-2-methyl-cyclohexanone (2a). An oven-dried 250 mL round-bottom flask equipped with a magnetic stir bar was fitted with a rubber septum and cooled to room temperature under an atmosphere of argon. To the flask were added Pd(OAc)$_2$ (3.37 mg, 15 µmol, 0.150 mol %) and (S)-t-BuPHOX (58 mg, 150 µmol, 1.50 mol %). The flask was evacuated and backfilled with argon three times. TBME (90 mL) was added to the flask and the mixture was stirred for 30 min in a 40° C. oil bath. Substrate 1a (1.96 g, 10.0 mmol, 1.0 equiv) was taken up in TBME (10 mL) and added to the stirring catalyst solution. The reaction was stirred for 16 h at 60° C., the reaction mixture was passed through a pad of silica gel (2 cm diameter×3 cm height) and rinsed with diethyl ether (50 mL). The filtrate was concentrated in vacuo and the remaining oil was distilled through a short path apparatus (bp. 91-93° C./16 mmHg) into a receiving flask immersed in an ice water bath to yield product 2a as a pale yellow oil (1.45 g, 9.50 mmol, 95% yield). The product was determined to be in 89% ee by chiral GC and matched previously reported characterization data.

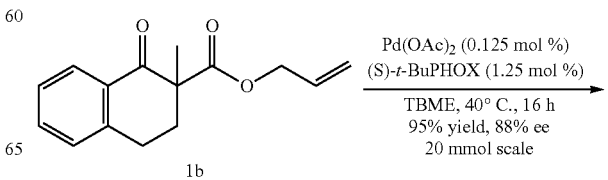

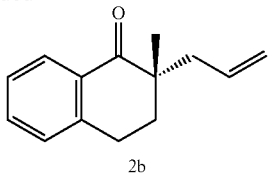

(S)-2-allyl-2-methyl-3,4-dihydronaphthalen-1(2H)-one (2b). An oven-dried 500 mL round-bottom flask equipped with a magnetic stir bar was fitted with a rubber septum and cooled to room temperature under an atmosphere of argon. To the flask were added Pd(OAc)$_2$ (5.6 mg, 25 μmol, 0.125 mol %) and (S)-t-BuPHOX (97 mg, 250 μmol, 1.25 mol %). The flask was evacuated and backfilled with argon three times. TBME (190 mL) was added to the flask and the mixture was stirred for 30 min in a 40° C. oil bath. Substrate 1b (4.89 g, 20.0 mmol, 1.0 equiv) was taken up in TBME (10 mL) and added to the stirring catalyst solution. The reaction was stirred for 16 h, concentrated in vacuo and purified by column chromatography (SiO$_2$, 5-10-20% Et$_2$O/hexanes) to yield product 2b as a pale yellow oil (3.81 g, 19.0 mmol, 95% yield). The product was determined to be in 88% ee by chiral SFC and matched previously reported characterization data.

REFERENCES 1. a) I. Denissova, L. Barriault, *Tetrahedron* 2003, 59, 10105-10146; b) C. J. Douglas, L. E. Overman, *Proc. Natl. Acad. Sci. U.S.A.* 2004, 101, 5363-5367; c) J. Christoffers, A. Baro, *Adv. Synth. Catal.* 2005, 347, 1473-1482; d) B. M. Trost, C. Jiang, *Synthesis* 2006, 369-396; e) P. G. Cozzi, R Hilgraf, N. Zimmermann, *Eur. I Org. Chem.* 2007, 36, 5969-5994.
2. a) J. T. Mohr, B. M. Stoltz, *Chem. Asian. J.* 2007, 2, 1476-1491. b) Y. Liu, S.-J. Han, W.-B. Liu, B M. Stoltz, *Acc. Chem. Res.* 2015, 48, in press. DOI: 10.1021/ar5004658.
3. For examples of the enantioselective allylic alkylation of enolates catalyzed by palladium, see: a) B. M. Trost, J. Xu, T. Schmidt, *J. Am. Chem. Soc.* 2009, 131, 18343-18357; b) B. M. Trost, B. Schäffner, M. Osipov, D. A. A. Wilton, *Angew. Chem.* 2011, 123, 3610-3613; *Angew. Chem. Int. Ed.* 2011, 50, 3548-3551; c) M. Nakamura, A. Hajra, K. Endo, E. Nakamura, *Angew. Chem.* 2005, 117, 7414-7417; *Angew. Chem. Int. Ed.* 2005, 44, 7248-7251; d) É. Bélanger, K. Cantin, O. Messe, M. Tremblay, J.-F. Paquin, *J. Am. Chem. Soc.* 2007, 129, 1034-1035; e) É. Bélanger, C. Houzé, N. Guimond, K. Cantin, J.-F. Paquin, *Chem. Commun.* 2008, 3251-3253; f) E. C. Burger, J. A. Tunge, *Org. Lett.* 2004, 6, 4113-4115; g) K. Chattopadhyay, R. Jana, V. W. Day, J. T. Douglas, J. A. Tunge, *Org. Lett.* 2010, 12, 3042-3045.
4. a) D. H. B. Ripin, D. E. Bourassa, T. Brandt, M. J. Castaldi, H. N. Frost, J. Hawkins, P. H. Johnson, S. S. Massett, K. Neumann, J. Phillips, J. W. Raggon, P. R. Rose, J. L. Rutherford, B. Sitter, A. M. Stewart, III; M. G. Vetelino, L. Wei, *Org. Process Res. Dev.* 2005, 9, 440-450; b) X. Jiang, G. T. Lee, K. Prasad, O. Repic, *Org. Process Res. Dev.* 2008, 12, 1137-1141; c) S. Caron, E. Vazquez, R. W. Stevens, K. Nakao, H. Koike, Y. Murata, *J. Org. Chem.* 2003, 68, 4104-4107; d) B. P. Chekal, S. M. Guinness, B. M. Lillie, R. W. McLaughlin, C. W. Palmer, R. J. Post, J. E. Sieser, R. A. Singer, G. W. Sluggett, R. Vaidyanathan, G. J. Withbroe, *Org. Process Res. Dev.* 2014, 18, 266-274; e) J. Magano, J. R. Dunetz, *Chem. Rev.* 2011, 111, 2177-2250; f) K. Konigsberger, G. P. Chen, R. R. Wu, M. J. Girgis, K. Prasad, O. Repic, T. J. Blacklock, *Org. Process Res. Dev.* 2003, 7, 733-742.
5. A. O. King, N. Yasuda *Palladium-Catalyzed Cross-Coupling Reactions in the Synthesis of Pharmaceuticals* in *Organometallics in Process Chemistry*, (Ed.: R. D. Larsen), Springer, Berlin, Germany, 2004, pp 205-246.
6. a) J. A. Keith, D. C. Behenna, J. T. Mohr, S. Ma, S. C. Marinescu, J. Oxgaard, B. M. Stoltz, W. A. Goddard III, *J. Am. Chem. Soc.* 2007, 129, 11876-11877; b) N. H. Sherden, D. C. Behenna, S. C. Virgil, B. M. Stoltz, *Angew. Chem.* 2009, 121, 6972-6975; *Angew. Chem. Int. Ed.* 2009, 48, 6840-6843; c) J. A. Keith, D. C. Behenna, N. Sherden, J. T. Mohr, S. Ma, S. C. Marinescu, R. J. Nielsen, J. Oxgaard, B. M. Stoltz, W. A. Goddard III, *J. Am. Chem. Soc.* 2012, 134, 19050-19060.
7. a) K. Tani, D. C. Behenna, R. M. McFadden, B. M. Stoltz, *Org. Lett.* 2007, 9, 2529-2531; b) M. R. Krout, J. T. Mohr, B. M. Stoltz, *Org. Synth.* 2009, 86, 181-193.
8. N. T. McDougal, J. Streuff, H. Mukherjee, S. C. Virgil, B. M. Stoltz, *Tetrahedron Lett.* 2010, 51, 5550-5554.
9. a) P. J. Dunn, in *Pharmaceutical Process Development*, (Eds.: J. A. Blacker, M. T. Williams), Royal Society of Chemistry, London, 2011, Chapter 6; b) *Green Chemistry and Engineering: A Practical Approach*, (Eds.: C. Jimenez-Gonzales, D. J. Constable), Wiley, New York, 2011.
10. a) P. G. Jessop, *Green Chem.* 2011, 13, 1391-1398; b) C. Capello, U. Fischer, K. Hungerbühler, *Green Chem.* 2007, 9, 927-934.
11. D. C. Behenna, Y. Lu; T. Yurino, J. Kim, D. E. White, S. C. Virgil, B. M. Stoltz, *Nature Chem.* 2012, 4, 130-133.
12. J. A. Enquist Jr., B. M. Stoltz, *Nature* 2008, 453, 1228-1231.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:
1. A method for the preparation of a compound of formula (Ia):

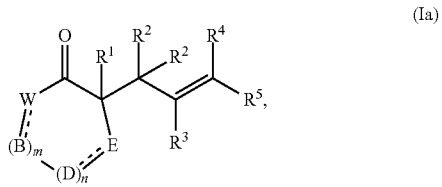

comprising treating a compound of formula (IIa) or (IIIa): or a salt thereof;

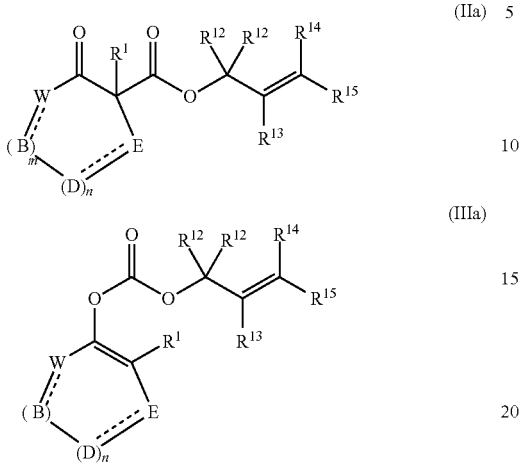

with a Pd(II) catalyst, wherein the Pd(II) catalyst is used in an amount from about 0.02 mol % to about 1 mol % relative to the compound of formula (IIa) or of formula (IIIa), and wherein, as valence and stability permit, $R^1$ represents substituted or unsubstituted alkyl, alkenyl, alkynyl, aralkyl, aryl, (5- to 10-membered heteroaryl) alkyl, 5- to 10-membered heteroaryl, or halo;

$R^2$, $R^3$, $R^4$, $R^5$, $R^{12}$, $R^{13}$, $R^{14}$, and $R^{15}$ are independently selected for each occurrence from hydrogen, and alkyl;

W represents —$NR^6$—;

B, D, and E independently for each occurrence represent, as valence permits, $CR^7R^8$, C(O) or $CR^7$;

$R^6$ represents hydrogen or optionally substituted alkyl, cycloalkyl, (cycloalkyl)alkyl, aryl, aralkyl, 5- to 10-membered heteroaryl, (5- to 10-membered heteroaryl)alkyl, alkenyl, alkynyl, —C(O)alkyl, —C(O) aryl, —C(O)aralkyl, —C(O)heteroaryl, —C(O)—(5- to 10-membered heteroaryl)alkyl, —C(O)O(alkyl), —C(O)O(aryl), —C(O)O(aralkyl), —C(O)O(heteroaryl), or —C(O)O—(5- to 10-membered heteroaryl)alkyl;

$R^7$ and $R^8$ each independently represent hydrogen, hydroxyl, halogen, nitro, alkyl, cycloalkyl, (cycloalkyl)alkyl, aryl, aralkyl, heteroaryl, (5- to 10-membered heteroaryl)alkyl, (3- to 10-membered heterocyclyl)alkyl, 3- to 10-membered heterocyclyl, alkenyl, alkynyl, cyano, carboxyl, sulfate, amino, alkoxy, arylalkoxy, alkylamino, alkylthio, hydroxyalkyl, alkoxyalkyl, aminoalkyl, mercaptoalkyl, ether group, thioether group, ester group, amido, thioester group, carbonate group, carbamate group, urea group, sulfonate group, sulfone group, sulfoxide group, sulfonamide group, acyl, acyloxy, or acylamino;

each occurrence of ═ independently represents a double bond or a single bond as permitted by valence; and m and n are integers wherein the sum of m and n is 2;

wherein each heteroaryl or heterocyclyl comprises 1 to 4 heteroatoms selected from N, O, and S;

wherein substituents on the alkyl, haloalkyl, alkenyl, alkynyl, aralkyl, aryl, (5- to 10-membered heteroaryl) alkyl, 5- to 10-membered heteroaryl, (cycloalkyl)alkyl, cycloalkyl, cycloalkenyl, (3- to 10-membered heterocyclyl)alkyl, 3- to 10-membered heterocyclyl, alkoxy, or amino are selected from a halogen group, hydroxyl, carboxyl, alkoxycarbonyl, formyl, acyl, thioester group, thioacetate group, thioformate group, alkoxy, phosphate group, phosphonate group, phosphinate group, amino, amido, amidine group, imine group, cyano, nitro, azido, sulfhydryl, mercaptoalkyl, sulfate group, sulfonate group, sulfamoyl, sulfonamido, sulfonyl, 5- to 10-membered heterocyclyl, aralkyl, aromatic group, and 5- to 10-membered heteroaromatic group.

2. A method for the preparation of a compound of formula (Ia):

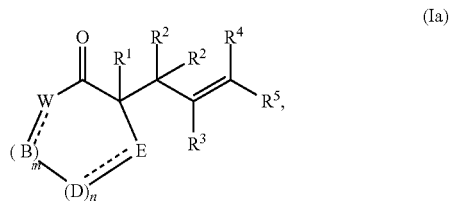

comprising treating a compound of formula (IVa) or (Va) or a salt thereof:

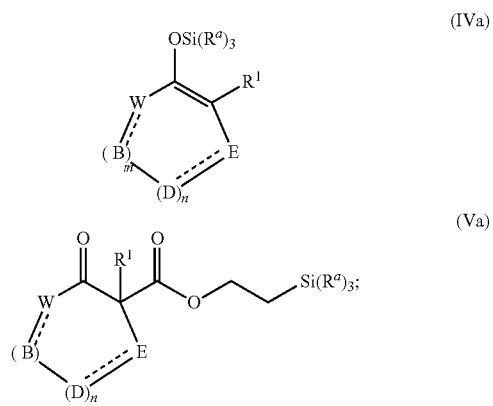

with a compound of formula (X):

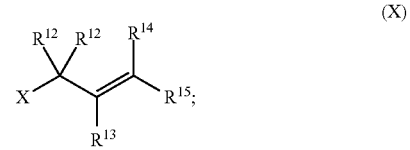

and a Pd(II) catalyst, wherein the Pd(II) catalyst is used in an amount from about 0.02 mol % to about 1 mol % relative to the compound of formula (IVa) or of formula (Va), and wherein, as valence and stability permit, $R^1$ represents substituted or unsubstituted alkyl, alkenyl, alkynyl, aralkyl, aryl, (5- to 10-membered heteroaryl) alkyl, 5- to 10-membered heteroaryl, or halo;

$R^2$, $R^3$, $R^4$, $R^5$, $R^{12}$, $R^{13}$, $R^{14}$, and $R^{15}$ are independently selected for each occurrence from hydrogen, and alkyl;

W represents —$NR^6$—;

B, D, and E independently for each occurrence represent, as valence permits, $CR^7R^8$, C(O) or $CR^7$;

$R^6$ represents hydrogen or optionally substituted alkyl, cycloalkyl, (cycloalkyl)alkyl, aryl, aralkyl, heteroaryl, (5- to 10-membered heteroaryl)alkyl, alkenyl, alkynyl, —C(O)alkyl, —C(O)aryl, —C(O)aralkyl, —C(O)heteroaryl, —C(O)—(5- to 10-membered heteroaryl)alkyl, —C(O)O(alkyl), —C(O)O(aryl), —C(O)O(aralkyl), —C(O)O(heteroaryl), —C(O)O—(5- to 10-membered heteroaryl)alkyl;

$R^7$ and $R^8$ each independently represent hydrogen, hydroxyl, halogen group, nitro, alkyl, cycloalkyl, (cycloalkyl)alkyl, aryl, aralkyl, heteroaryl, (5- to 10-membered heteroaryl)alkyl, (3- to 10-membered heterocyclyl)alkyl, 3- to 10-membered heterocyclyl, alkenyl, alkynyl, cyano, carboxyl, sulfate group, amino, alkoxy, arylalkoxy, alkylamino, alkylthio, hydroxyalkyl, alkoxyalkyl, aminoalkyl, mercaptoalkyl, ether group, thioether group, ester group, amido, thioester group, carbonate group, carbamate group, urea group, sulfonate group, sulfone group, sulfoxide group, sulfonamide group, acyl, acyloxy, or acylamino;

or any two occurrences of $R^6$, $R^7$, and $R^8$ on adjacent W, B, D, or E groups, taken together with the intervening atoms, form an optionally substituted aryl, 5- to 10-membered heteroaryl, cycloalkyl, cycloalkenyl, 3- to 10-membered heterocyclyl, or (3- to 10-membered heterocyclyl)alkenyl group;

each occurrence of $=\!=\!=$ independently represents a double bond or a single bond as permitted by valence;

m and n are integers each independently selected from 0, 1, and 2;

$R^a$ represents optionally substituted alkyl, aryl, or alkoxyl; and

X represents a halide group, carbonate group, sulfonate group, acetate group, or carboxylate group;

wherein each heteroaryl or heterocyclyl comprises 1 to 4 heteroatoms selected from N, O, and S;

wherein substituents on the alkyl, haloalkyl, alkenyl, alkynyl, aralkyl, aryl, (5- to 10-membered heteroaryl)alkyl, 5- to 10-membered heteroaryl, (cycloalkyl)alkyl, cycloalkyl, cycloalkenyl, (3- to 10-membered heterocyclyl)alkyl, 3- to 10-membered heterocyclyl, alkoxy, or amino are selected from a halogen group, hydroxyl, carboxyl, alkoxycarbonyl, formyl, acyl, thioester group, thioacetate group, thioformate group, alkoxy, phosphate group, phosphonate group, phosphinate group, amino, amido, amidine group, imine group, cyano, nitro, azido, sulfhydryl, mercaptoalkyl, sulfate group, sulfonate group, sulfamoyl, sulfonamido, sulfonyl, 3- to 10-membered heterocyclyl, aralkyl, aromatic group, and 3- to 10-membered heteroaromatic moiety.

3. The method of claim 1, wherein at least two adjacent occurrences of B, D, and E are —$CR^7$—.

4. The method of claim 1, wherein $R^6$ represents, independently for each occurrence, hydrogen or optionally substituted alkyl, aralkyl, (5- to 10-membered heteroaryl)alkyl, —C(O)alkyl, —C(O)aryl, —C(O)aralkyl, —C(O)O(alkyl), —C(O)O(aryl), or —C(O)O(aralkyl).

5. The method of claim 1, wherein $R^2$, $R^3$, $R^4$, $R^5$, $R^{12}$, $R^{13}$, $R^{14}$, and $R^{15}$ are each hydrogen.

6. The method of claim 1, wherein $R^1$ represents unsubstituted alkyl, alkenyl, alkynyl, aralkyl, aryl, (5- to 10-membered heteroaryl)alkyl, 5- to 10-membered heteroaryl, or halo.

7. The method of claim 1, wherein the Pd(II) catalyst is selected from $Pd(OC(O))R^c)_2$, $Pd(OAc)_2$, $PdCl_2$, $Pd(PhCN)_2Cl_2$, $Pd(CH_3CN)_2Cl_2$, $PdBr_2$, $Pd(acac)_2$, $[Pd(allyl)Cl]_2$, $Pd(TFA)_2$, and pre-formed Pd(II)-ligand complex;

wherein $R^c$ is optionally substituted alkyl, alkenyl, alkynyl, aryl, heteroaryl, aralkyl, (5- to 10-membered heteroaryl)alkyl, cycloalkyl, 5- to 10-membered heterocyclyl, (cycloalkyl)alkyl, or (5- to 10-membered heterocyclyl)alkyl.

8. The method of claim 1, wherein the Pd(II) catalyst is $Pd(OAc)_2$.

9. The method of claim 1, wherein the Pd(II) catalyst further comprises a chiral ligand.

10. The method of claim 9, wherein the chiral ligand is used in an amount from about 0.1 mol % to about 100 mol % relative to the compound of formula (IIa).

11. The method of claim 1 further comprising an organic solvent selected from methyl tert-butyl ether, toluene, and 2-methyltetrahydrofuran.

12. The method of claim 1, whereby the compound of formula (Ia) is enantioenriched.

\* \* \* \* \*

UNITED STATES PATENT AND TRADEMARK OFFICE
CERTIFICATE OF CORRECTION

PATENT NO. : 10,106,479 B2
APPLICATION NO. : 15/081157
DATED : October 23, 2018
INVENTOR(S) : Brian M. Stoltz et al.

It is certified that error appears in the above-identified patent and that said Letters Patent is hereby corrected as shown below:

In the Claims

Claim 1, seventh line, Formula (IIIa), should read -- 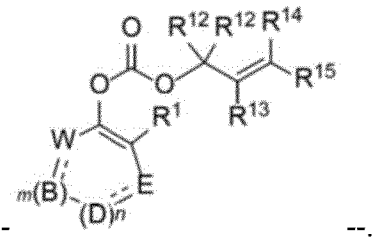 --.

Claim 2, seventh line, Formula (Va), should read -- 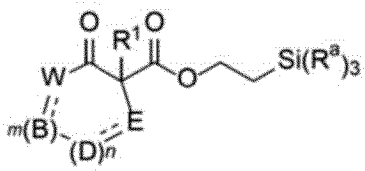 --.

Claim 7, second line, "Pd(OC(O))R$^c$)$_2$," should read --Pd(OC(O)R$^c$)$_2$,--.

Signed and Sealed this
Twentieth Day of August, 2019

Andrei Iancu
*Director of the United States Patent and Trademark Office*